US006414032B1

(12) United States Patent
Johnson

(10) Patent No.: US 6,414,032 B1
(45) Date of Patent: Jul. 2, 2002

(54) ANTI-INFECTIVE COMPOSITIONS FOR TREATING DISORDERED TISSUE SUCH AS COLD SORES

(76) Inventor: B. Ron Johnson, 4061 Canyon View Pl., Sandy, UT (US) 84092

(*) Notice: Subject to any disclaimer, the term of this patent is extended or adjusted under 35 U.S.C. 154(b) by 0 days.

(21) Appl. No.: 09/668,951

(22) Filed: Sep. 22, 2000

Related U.S. Application Data

(63) Continuation-in-part of application No. 09/401,076, filed on Sep. 22, 1999, now Pat. No. 6,211,243.

(51) Int. Cl.⁷ .................. A61K 31/155; A61K 31/24; A61K 31/045
(52) U.S. Cl. .................. 514/634; 514/535; 514/724
(58) Field of Search ................ 514/634, 724, 514/535

(56) References Cited

U.S. PATENT DOCUMENTS

| | | | |
|---|---|---|---|
| 1,822,566 A | 9/1931 | Davies | |
| 3,369,543 A | 2/1968 | Ronco | 128/269 |
| 4,183,684 A | 1/1980 | Avery, Jr. | 401/133 |
| 4,262,007 A | 4/1981 | Sherrill | 424/274 |
| 4,390,539 A | 6/1983 | Sherrill | 424/251 |
| 4,394,381 A | 7/1983 | Sherrill | 424/274 |
| 4,486,450 A | 12/1984 | Bernstein | |
| 4,507,281 A | 3/1985 | Asculai et al. | 424/85 |
| 4,661,354 A | 4/1987 | Finnerty | 424/145 |
| 4,822,605 A | 4/1989 | Powell | 424/85.2 |
| 4,828,542 A | 5/1989 | Hermann | 604/3 |
| 4,875,602 A | 10/1989 | Chickering et al. | 222/187 |
| 4,887,994 A | 12/1989 | Bedford | 601/1 |
| 4,895,727 A | 1/1990 | Allen | 424/642 |
| 4,929,442 A | 5/1990 | Powell | 424/85.2 |
| 4,952,204 A | 8/1990 | Korteweg | 604/1 |
| 4,957,734 A | 9/1990 | Miller | 424/107 |
| 4,975,217 A | 12/1990 | Brown-Skrobot et al. | 252/107 |
| 5,016,651 A | 5/1991 | Stalcup et al. | 128/898 |
| 5,036,095 A | 7/1991 | Andermann | 514/389 |
| 5,137,724 A | 8/1992 | Balzarini et al. | 424/400 |
| 5,198,217 A | 3/1993 | Vedros | 424/195.1 |
| 5,387,611 A | 2/1995 | Rubinstein | |
| 5,405,602 A | 4/1995 | Simmons et al. | 424/47 |
| 5,439,685 A | 8/1995 | Augros | 424/430 |
| 5,503,853 A | 4/1996 | Bollen et al. | 424/430 |
| 5,527,534 A | 6/1996 | Myhling | 424/430 |
| 5,631,245 A | 5/1997 | Drube | 514/62 |
| 5,637,307 A | 6/1997 | Simmons et al. | 424/390 |
| 5,661,170 A | 8/1997 | Chodosh | 514/390 |
| 5,678,273 A | 10/1997 | Porcelli | |
| 5,704,906 A | 1/1998 | Fox | 604/1 |
| 5,709,866 A | 1/1998 | Booras et al. | 424/400 |
| 5,712,257 A | 1/1998 | Carter | 514/44 |
| 5,725,875 A | 3/1998 | Noll et al. | 424/44 |
| 5,753,270 A | 5/1998 | Beauchamp et al. | 424/667 |
| 5,762,940 A | 6/1998 | Bourbon et al. | 424/217.1 |
| 5,767,163 A | 6/1998 | Kundsin | |
| 5,827,870 A | 10/1998 | Chodosh | 514/390 |
| 5,906,814 A | 5/1999 | Epstein | |
| 5,948,822 A | 9/1999 | Pope et al. | |
| 5,952,392 A | 9/1999 | Katz et al. | |
| 6,211,243 B1 * | 4/2001 | Johnson | 514/634 |

FOREIGN PATENT DOCUMENTS

| | | | |
|---|---|---|---|
| CA | 2143136 | 8/1996 | |
| EP | 0 181 184 | 5/1986 | |
| EP | 0 190 797 | 8/1986 | |
| FR | 2 700 698 | 7/1994 | |
| GB | 1 479 480 | 7/1977 | |
| WO | WO 98/11778 | 3/1998 | A01N/33/12 |
| WO | WO 98/42188 | 10/1998 | A01N/33/12 |
| WO | WO 99/08713 | 2/1999 | |

OTHER PUBLICATIONS

AHFS Drug Information, pp. 3107–3108, 1999.
Physicians Desk Reference for Non–Prescription Durgs, Product Information, pp. 643, 644, 649, 503, 507, and reference pages to Bactine, and Tanac, 1998.
Winthrop Laboratories, Zephiran® Chloride, informational Brochure, Jul. 1980.
Encyclopedia Brittanica, Inc., Defnitions of Skin and Skin, Diseases Of, pp. 603–609, 1970.
DentalDots® What are they?, located at "http://www.dentaldots.com/whatsadot.htm," page 1, web page dated Jul. 14, 1999.
ViraMedx/Really Fast Relief for Herpes Related Outbreaks, located at "http://www.viramedx.com/," 1 page, web page dated Jun. 28, 1999.
Cold Sores Healed in Less than 24 Hours Report Says, located at "http://www.viramedx.com/news01.htm," 2 pages, web page dated Jun. 28, 1999.
Comparison of Zovirax, Valtrex, Famvir and VirMedx, located at "http://www.viramedx.com/compar..htm," 1 page, web page dated Jun. 28, 1999.
Herpes Treatment That Works on Genital Herpes Too, located at "http://www.viramedx.com/about.htm," 1 page, web page dated Jun. 28, 1999.

(List continued on next page.)

Primary Examiner—Kevin E. Weddington
(74) Attorney, Agent, or Firm—Workman, Nydegger, Seeley

(57) ABSTRACT

The present invention relates to the treatment of disordered epithelial tissues such as cold sores and other complications resulting from disorders such as herpes, and the like. The invention relates to the use of an anti-infective and/or antimicrobial active agent in a carrier, with vigorous agitation of the disordered epithelial tissue for topical treatment thereof under such conditions sufficient to achieve clinically discernable improvement of the disordered epithelial tissue. The preferred anti-infective and/or antimicrobial active agent is an organohalide such as a quaternary ammonium compound, preferably benzalkonium chloride. The inventive method may be used also in connection with a preferred applicator configuration.

51 Claims, 9 Drawing Sheets

OTHER PUBLICATIONS

Herpes Treatment Shows Promise Against Genital Herpes, located at "http://www.viramedx.com/study.htm," 1 page, web page dated Jun. 28, 1999.

Results Against Clinical Strains of Herpes Simplex Virus, located at "http://www.ciramedx.com/labdata.htm," 1 page, web page dated Jun. 28, 1999.

8 Year Study to Determine Effectiveness Against Herpes, located at "http://www.viramedx.com/clinicaldata.htm," 1 page, web page dated Jun. 28, 1999.

8 Year Study to Determine Effectiveness Against Herpes, located at "http://www.ciramedx.com/results.htm," 5 pages, web page dated Jun. 28, 1999.

8 Year Study to Determine Effectiveness Against Herpes, located at "http://www.viramedx.com/clinicalsum.htm," 2 pages, web page dated Jun. 28, 1999.

Sigma Product Information Sheet, Benzalkonium Chloride, located at http://www.sigma.sial.com/sigma/proddata/b1383.htm.

ViraMedix, Antiviral Activity of Viracea® Against Acyclovir Resistant Strains of Herpes Simplex Virus (HSV), located at "http://www.herpescontrol.com/acyresist.htm," by K.D. Thompson et al., The University of Chicago and Meryx Pharmaceutical, Chicago, Il (study results found at http://www.herpescontrol.com/figure3.htm), © 1998.

ViraMedix News Release, Announcing the First OTC Treatment Proven to "Kill" the Herpes Virus that Causes Cold Sores, Fever Blisters and Related Outbreaks, Healing the Outbreak in Usually Less than 24 Hours/Timely Introduction in Light of Recent News of the Spread of Herpes Caused Outbreaks and Just in Time for the Summer Sun Caused Outbreaks of Cold Sores, located at http://www.herpescontrol.com/news01.htm, © 1998.

Study Results, Testimonials, located at http://www.herpescontrol.com/results.htm, © 1998.

Berti, et al., Transcutaneous Drug Delivery: A Practical Review, *Mayo Clin. Proc.*, vol. 70, pp. 581–586, Jun. 1995.

Choi, et al., The Pretreatment Effect of Chemical Skin Penetration Enhancers in Transdermal Drug Delivery Using Iontophoresis, *Skin Pharmacol. Appl. Skin Physiol.*, pp. 326–335, 1999.

Comfort et al., Enhanced Transport in a Therapeutic Transdermal System, *Biomaterials*, vol. 11, No. 9, pp. 729–733, Nov. 1990.

Fang et al., Development and Evaluation on Transdermal Delivery of Enoxacin Via Chemical Enhancers and Physical Iontophoresis, *Journal of Controlled Release*, vol. 54, pp. 293–304, 1998.

Fang et al., Evaluation of Transdermal Iontophoresis of Enoxacin From Polymer Formulations: In Vitro Skin Permeation and In Vivo Microdialysis Using Wistar Rat as an Animal Model, *International Journal of Pharmaceutics 180*, pp. 137–149, 1999.

Gismondo, et al., Efficacia Antimicrobica e Sporicida di Varie Soluzioni Disinfettanti, *Minerva Medica*, (Italy) vol. 86, pp. 21–32, Jan.–Feb. 1995 (English translation attached: Antimicrobial and Sporicidal Efficacy of Some Disinfectant Solutions).

James Alexander Croporation flyer, *Medicaine® Sting and Bite Relief Formula Flyer*, 1997.

James Alexander Corporation flyer, *Medicaine® Topical Antiseptic*, 1997.

James Alexander Corporation flyer, *Unit Dose Swabs*, 1997.

Jin et al., Effect of Application Volume of Ethanol–Isopropyl Myristate Mixed Solvent System on Permeation of Zidovudine and Probenecid Through Rat Skin, *Drug Development and Industrial Pharmacy*, vol. 26 No. 2, pp. 193–198, 2000.

Johnson, et al., Supergistic Effects of Chemical Enhancers and Therapeutic Ultrasound on Transdermal Drug Delivery, *Journal of Pharmaceutical Sciences*, vol. 85, No. 7, pp. 670–679, Jul. 1996.

Kanikkannan, et al., Structure–Activity Relationship of Chemical Penetration Enhancers in Transdermal Drug Delivery, Current Medicinal Chemistry, vol. 7, No. 6, pp. 593–608, 2000.

Martindale, The Extra Pharmacopoeia, Benzethonium Chloride–Benzyl Alcohol, p. 1119, Royal Pharmaceutical Society, 1996.

Martindale, The Extra Pharmacopoeia, *Disinfectants and Preservatives*, pp. 1114–1116, Royal Pharmaceutical Society, 1996.

Martindale, The Extra Pharmacopoeia, Ethyl Hydroxybenxoate/Magenta, p. 1137, Royal Pharmaceutical Society, 1996.

Martindale, The Extra Pharmacopoeia, Local Anesthetics, pp. 1317, 1320–1321, Royal Pharmaceutical Society, 1996.

The Merck Index, An Encyclopedia of Chemicals, drugs, and Biologicals, Twelfth Edition, pp. 177 and 180, 1996.

Meyler's Side Effects of Drugs, an Encyclopedia of Adverse Reactions and Interactions, *Antiseptic Drugs and Disinfectants*, Chapter 24, pp. 643–644 and 664–665, 1996.

Sanofi Pharmaceuticals, Inc., Zephiran® Chloride, Brand of Benzalkonium Chloride, 1997.

Williams, et al., Skin Absorption Enhancers, *Critical Reviews in Therapeutic Drug Carrier Systems*, 9(3,4), pp. 305–353, 1992.

Wu et al., In Vitro Effect of Penetration Enhancers on Sodium Nonivamide Acetate in Rat Skin, *Biol. Pharm. Bull.*, vol. 18, No. 12, pp. 1790–1792, 1995.

* cited by examiner

ANTI-INFECTIVE COMPOSITIONS FOR TREATING DISORDERED TISSUE SUCH AS COLD SORES

RELATED APPLICATIONS

This application is a continuation-in-part of U.S. patent application Ser. No. 09/401,076 which was filed on Sep. 22, 1999 U.S. Pat. No. 6,211,243 for B. Ron Johnson. The amended title of Ser. No. 09/401,076 is METHODS FOR TREATING COLD SORES WITH ANTI-INFECTIVE COMPOSITIONS DELIVERED WITH VIGOROUS AGITATION. For purposes of disclosure of the present invention, Ser. No. 09/401,076 is incorporated herein by specific reference.

BACKGROUND OF THE INVENTION

1. The Field of the Invention

The present invention relates to the treatment of disordered tissue with anti-infective compositions especially antiviral and antimicrobial compositions. More particularly, the treatment compositions include quaternary amine medicament compounds or organochlorides. The present invention provides a novel combination of treatment compositions and modes of applying them to treat tissue disorders, particularly epithelial tissue disorders such as herpes infections.

2. The Relevant Technology

Tissue disorders, particularly those which impact epithelial tissue such as Herpes Simplex types I and II, candida albicans, acne, psoriasis, eczema, seborrhea, dermatitis, and pink eye are common and are often difficult to treat symptoms. Such disorders are more likely to develop in people living with compromised sanitary conditions, the elderly, and the chronically ill. Others susceptible to such disorders include workers in health care, agricultural workers, chemical industry workers, individuals working with industrial cleaners, and painters, where chronic exposure to chemicals, pathogens, and unsanitary conditions tend to weaken and irritate epithelial tissue.

Herpes simplex virus (HSV) and Herpes Zoraster, commonly referred to as "herpes virus" or "herpes," is an infectious disease which has reached crisis proportions nationally with estimated numbers of infected people at 70%–80% of U.S. population as reported by the American Social Health Association (ASHA) and growing annually by 500,000 people or more. There are two common types of herpes: herpes simplex virus 1 (HSV 1) and herpes simplex virus 2 (HSV 2).

Herpes enters the human body through minuscule breaks in the epidermal tissue usually by contact with an infected host and is marked by eruption of one or more vesicles, usually in groups, following an incubation period of approximately four to ten days. Typically the course of the infectious outbreak initiates with the prodromal stage; advancing to vesicular eruption; followed: by ulceration; coalescing; resolution; and the latency period. The outbreak can last for several weeks and on average lasts two to three weeks. In some immune compromised individuals, the outbreak can last for months. The vesicles can appear anywhere on epithelial tissues including the skin or mucosa, typically appearing on the lips as cold sores, glands, oral mucosa, conjunctiva and cornea, genitalia, anal mucosa and perianal tissue.

Herpes symptoms include: inguinal swelling, pain, fever, malaise, headaches, muscle aches, and swollen glands. Some individuals with oral herpes which impacts the trigeminal nerve, have excruciating facial pain, difficulty swallowing, eating and facial swelling. Individuals with the herpes which impacts the sacral nerve have severe upper leg pain, swelling, and great difficulty walking.

Herpes simplex virus (HSV) infection is recurring, residing in the nerve ganglia, then recurring due to some, as yet unknown, stimulus. Recurrent herpetic infections can be precipitated by almost anything, including: overexposure to sunlight; nutritional deficiencies; stress; menstruation; immunosuppression; certain foods; drugs; febrile illness; etc.

Herpes infections pose very serious health threats often causing: blindness; increased cancer risk of the cervix; aseptic meningitis and encephalitis; neonatal deaths; viremia; the spread of the human immunodeficiency virus (HIV); etc. The devastating effects of this disease, go well beyond the medical scope of human suffering; HSV is responsible for serious psychological and emotional distress as well as substantial economic loss.

Various treatments for herpes have been proposed and have included topical application of such agents as povidone-iodine, idoxuridine, trifluorothyidine, or acyclovir. Such treatments have met with varying degrees of success. Most prior treatments have proven disappointing. Acyclovir, an acyclic nucleoside, is taken orally for systemic treatment of HSV. Acyclovir is somewhat effective in inhibiting the activity of several herpes viruses. However, acyclovir is only successful in interrupting the replication of the virus and is used to treat infectious outbreak systemically. Denever is the topical version of acyclovir. Nothing to date has proven really effective topically. Strains resistant to acyclovir have been reported. Individuals with Auto Immune Deficiency Syndrome (AIDS) are seriously immune-compromised and suffer especially debilitating outbreaks of HSV. Additionally, AIDS individuals may carry acyclovir resistant strains of HSV, which can make acyclovir ineffective for these individuals. It is, therefore, of utmost importance to develop a safe and successful medical treatment to overcome the very serious problems of herpes virus.

Biologically active antiviral and microbial compositions have been met with marginal success when administered topically for tissue disorders. Such compositions have been applied as gels, creams, lotions, oils, ointments, pastes, tinctures, emulsions, and colloidal suspensions. Most of the compositions are oil-based to ensure that the composition has sufficient viscosity and/or tackiness to remain on the surface of the skin. In fact, such compositions are generally absorbed into clothing more than into the skin due to a relatively slow epidermal penetration rate. Even when applied to patients and time is available for the compositions to penetrate, they often were not sufficiently effective for one reason or another to substantially assist them in clearing up the disorder. Note that the FDA restricts the over-the-counter selling of compositions that do not remain on the surface of the skin for extended periods of time.

Many efforts have been undertaken to remedy the inadequate results of topically administered compositions having antiviral and antimicrobial qualities. The therapeutic effects of such compositions depend upon the specific active agent and the method of application. Many compositions of the prior art contain ingredients that may provide symptomatic relief of pain and itching, but none are claimed to be effective against Herpes infection except the drug, acyclovir, which is purported to have some topical efficacy. Additionally, most compositions intended to treat such disorders do not effectively treat the discomfort and the disease symptoms, let alone cure the disorder or put it into a significant remission.

Examples of conventional application methods and compositions are provided in WO 98/42188 and in WO 98/11778 by Squires, both of which are hereby incorporated by reference. In WO 98/42188 at page 9, lines 12–18 and in WO 98/11778 at page 5, lines 22–30, it is stated that the composition is applied by "spraying, dabbing, swabbing, sponging, brushing, pouring, dispensing, covering or heavily coating." The stated objective of these techniques for applying the composition is to insure that the composition remains on the infected area. Like other conventional treatment compositions, the composition has a viscosity and/or tackiness which enables it to remain on the surface of the infected area. A portion of such compositions may eventually penetrate beyond the surface of the disordered tissue such as the outer surface of skin or a lip, however, the viscosity of the composition combined with the application technique prevents such compositions from achieving effective penetration.

Another example of conventional application methods and compositions is provided in U.S. Pat. No. 5,753,270 issued to Beauchamp et al., which is also incorporated by reference. U.S. Pat. No. 5,732,270 discloses a composition which includes: (a) an antiseptic and/or anesthetic compound which is (i) a terpene such as menthol or eucalyptol, (ii) a phenolic compound such as thymol, or (iii) an alcohol such as menthol; (b) a quaternary ammonium antiseptic compound such as benzethonium chloride; and (c) an antiseptic compound containing iodine, salts thereof and/or complexes thereof dissolved in an organic skin penetrating solvent such as a mixture of water and acetone. The methodology is described in the examples provided at columns 5–7 as involving the liberal application of the composition to the afflicted area in a sequence such as 3 to 4 applications over a one minute period which is then repeated every 3 minutes over a 10 minute period. The entire procedure is then repeated after approximately ½ to 1 hour for 2 to 3 hours or until activity is stopped in healing is evident. The use of a cotton swab is mentioned at column 6, lines 10–11 for applying the composition.

Although it is mentioned in U.S. Pat. No. 5,753,270 at column 3, lines 44–49 that the formulations may be prepared as a gel, cream, a lotion, an ointment, or a paste the preferred embodiment appears to be a solution having an aqueous solvent system It is noted at column 3, lines 6–9 that although use of water and acetone as a solvent is preferred such a solvent is not considered essential to the overall synergistic action of the formulation. In any event, the formulation appears not to rely on either its viscosity or tackiness to ensure that the formation is maintained on the surface of the afflicted area as do most conventional compositions. Rather the methodology involves the very frequent reapplication of the formulation to the afflicted area. Some of the formulation may be absorbed into the skin, however, a significant portion is likely rapidly evaporated due to the high content of water and acetone.

The active agents disclosed in U.S. Pat. No. 5,753,270 which are discussed above include at least one compound which is an antiseptic and/or an anesthetic. The primary examples of such compounds: menthol, eucalyptol, and thymol are either obtained from natural sources such as naturally occurring oils or are derived from such oils. Eucalyptol is described as being an essential oil and a terpene ether. Thymol is derived from thyme oil or other oils. Menthol is obtained from peppermint oil or other oils. Other suitable compounds are also recited in the claims as including: eugenol, camphor, hexetidine or anethol. While the basis for inclusion of hexetidine in this grouping is not clear, the other chemicals are also obtained from natural sources or are derived therefrom. Eugenol is obtained by extraction of clove oil and then chemical modification. Camphor is a ketone which occurs naturally in the wood of the camphor tree. Anethol is derived from anise or fennel oils. While these compounds are useful, particularly as antifungal agents, it is doubtful that they assist in penetrating the afflicted tissue and may in fact retard or enhance the skin's natural resistance to penetration. The FDA does not consider these compounds as useful in the treatment of herpes, rather they are used for their softening effects.

In conclusion, significant medical research in this field of endeavor has been focused on developing compositions used for treating affected tissues and yet compositions which provide rapid relief to these ailments are still needed. It would therefore be an improvement in the art to provide a method of treating tissue disorders such as epithelial tissue disorders that overcome the problems of the prior art.

Such methods and systems of application are taught and claimed herein.

SUMMARY AND OBJECTS OF THE INVENTION

The present invention relates to the treatment of disordered tissue such as cold sores. An applicator may be used to apply a treatment composition comprising an anti-infective active agent in a carrier. The method may include vigorously agitating the disordered tissue treatment site with the applicator under conditions which are sufficient to enable the anti-infective active agent to rapidly penetrate the disordered tissue.

The present invention relates to the treatment of tissue disorders such as infections, particularly herpes related cold sores or other herpes disordered tissue. Throughout this disclosure, use of the term "disordered tissue" or "afflicted tissue", is understood to represent all tissue which has been affected by disorders such as, cold sores, all Herpes, *candida albicans,* acne, psoriasis, eczema, seborrhea, dermatitis, pink eye, shingles, and other predominantly viral disorders. Microbial and fungal infections are also types disordered tissues. Additionally, disordered tissue includes tissue which has been infected by venom as results from snake and spider bites, particularly venom infections from Brown Recluse spiders and Black Widow spiders.

It has been found that the therapeutic irritation of disordered tissue with a preferred treatment composition and the optional use of an applicator, stimulates rapid immunological attack and makes the composition and therapeutic irritation synergistically more effective. After the therapeutic irritation of the disordered tissue through vigorous rubbing and/or pressure, the treatment composition penetrates into the disordered tissue to enable the anti-infective active agent or agents to become chemically active much more deeply within the disordered tissue as compared to conventional application techniques.

In addition to the anti-infective active agent or agents, the composition also includes a carrier such as an alcohol. Oil and fatty carrier substances are preferably not added to the composition. Although various compositions have been applied to disordered tissue, the inventive methods and systems of vigorous irritation of the disordered tissue in connection with a preferred composition has extraordinary therapeutic effects. Consequently, the inventive compositions as well as the methods of application with vigorous irritation of disordered tissue provide effective methods of treatment.

The inventive systems utilize an applicator to deliver the treatment composition and most of the applicators can also be utilized to vigorously irritate disordered tissue to convey the inventive composition into the disordered tissue. The applicators allow the patient or a health professional to vigorously irritate the disordered tissue without cross-contamination from a dirty finger or the like. A finger may be used, of course, but it lacks the advantages of a sterile applicator, the absorbability of an applicator tip and the ability to irritate the skin surface in the desired manner. The applicator has the added advantage of directing focused pressure into the disordered tissue while the active compounds are expressed from the applicator into the disordered tissue. The combined effect of vigorous irritation of the disordered tissue and the administration of the inventive treatment compositions has the remarkable result of surprising therapeutic effects. Note that oils on the finger may react with the active agent and lessen its impact in the disordered tissue. For this same reason, moisturizing lotions should preferably not be applied to the treatment area after application of the treatment composition.

It is therefore an object of the present invention to provide a method for treating disordered tissue such as disordered portions of skin and mucous membranes. It is therefore an object of one embodiment of the present invention to provide a system for the treatment of epithelial tissue disorders that includes a preferred biologically anti-infective active composition and an applicator in connection with delivering the treatment composition and also preferably vigorously irritating the disorder site.

These and other objects and features of the present invention will become more filly apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to the treatment of disordered tissue with compositions that are any one or all of antiviral, antimicrobial, antifungal, or antivenomous. The compositions are rapidly absorbed into the disordered tissue. The efficacy of the compositions in penetrating the disordered tissue and initiating the restoration of the disordered tissue is enhanced by vigorously irritating the disordered tissue site. The disordered tissue is preferably vigorously agitated with an applicator. This is remarkably efficacious in causing the compositions to penetrate into disordered tissue and to stimulate the immune responses. Whether the anti-infective compositions are merely delivered onto the disordered tissue or delivered with vigorous irritation of the disordered tissue, the results are surprisingly advantageous in the treatment of epithelial tissue disorders.

Figure 1:
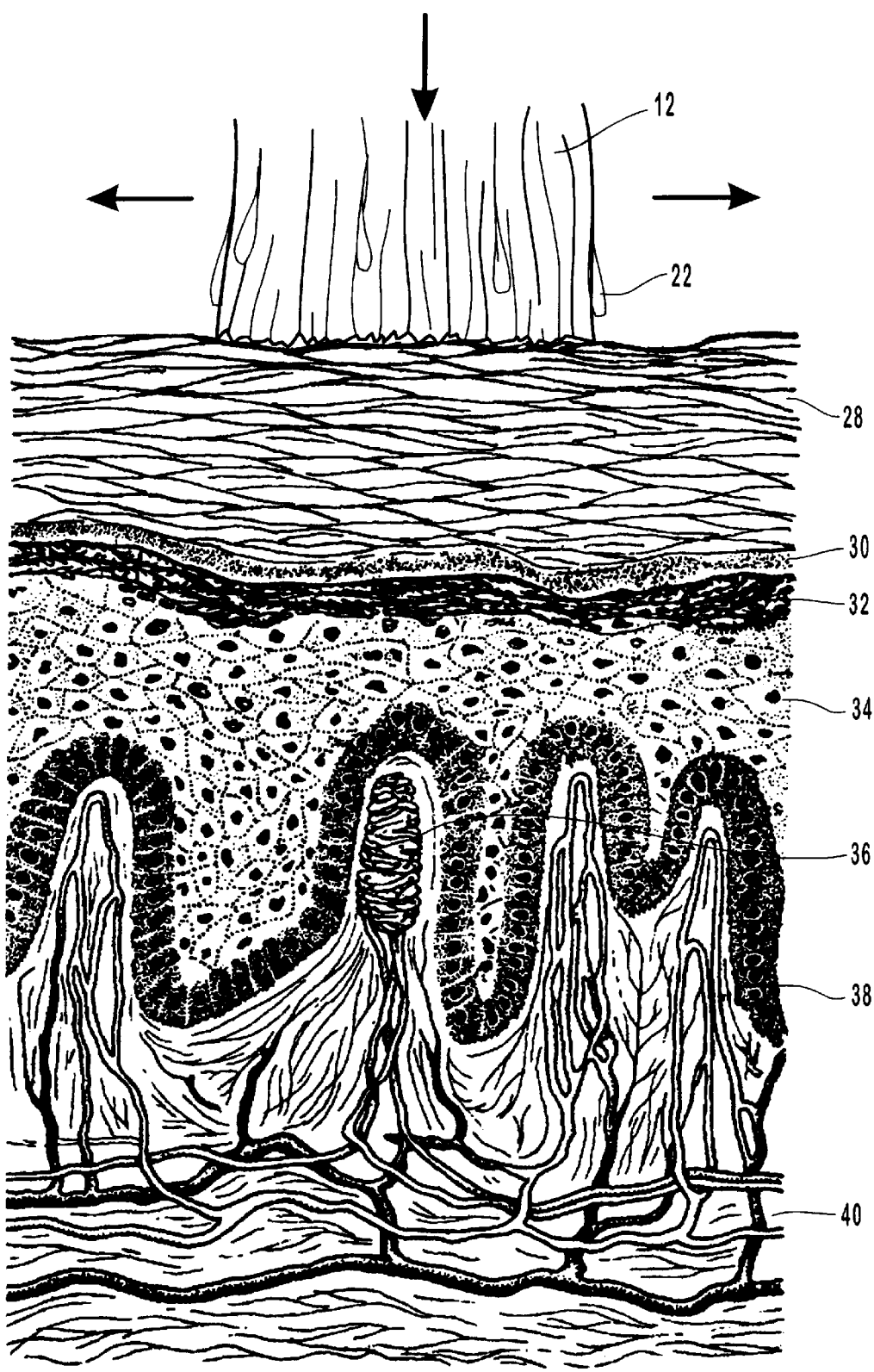
FIG. 1 is a vertical cross-section of the epidermis and the papillae of the dermis.
Figure 8:
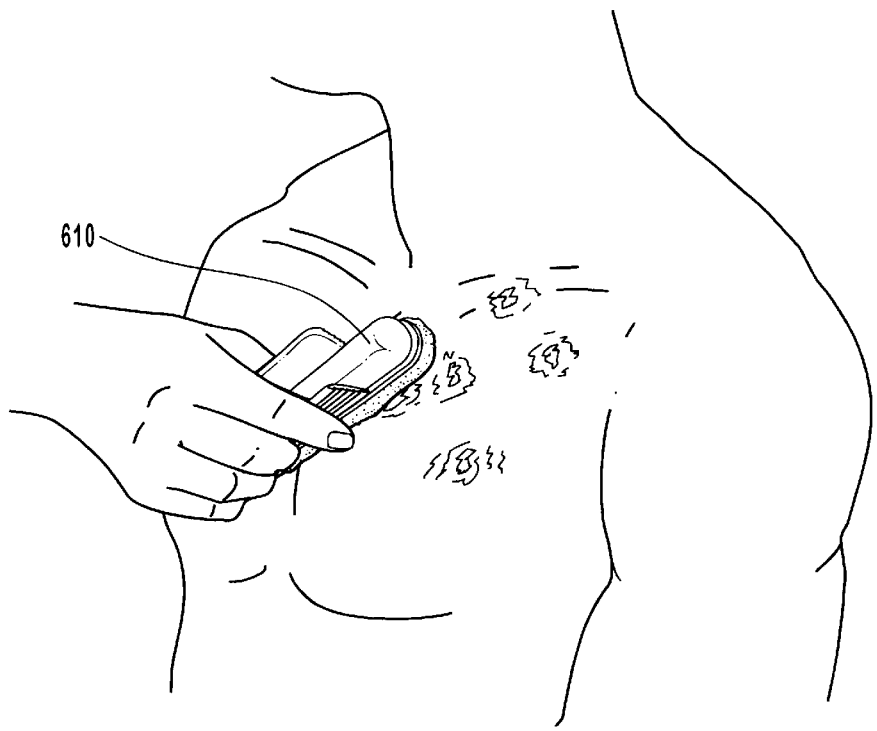
FIG. 8 is a perspective view of the alternative applicator in FIG. 7 being used to apply the treatment composition to sores from shingles on the chest area.
Figure 9:
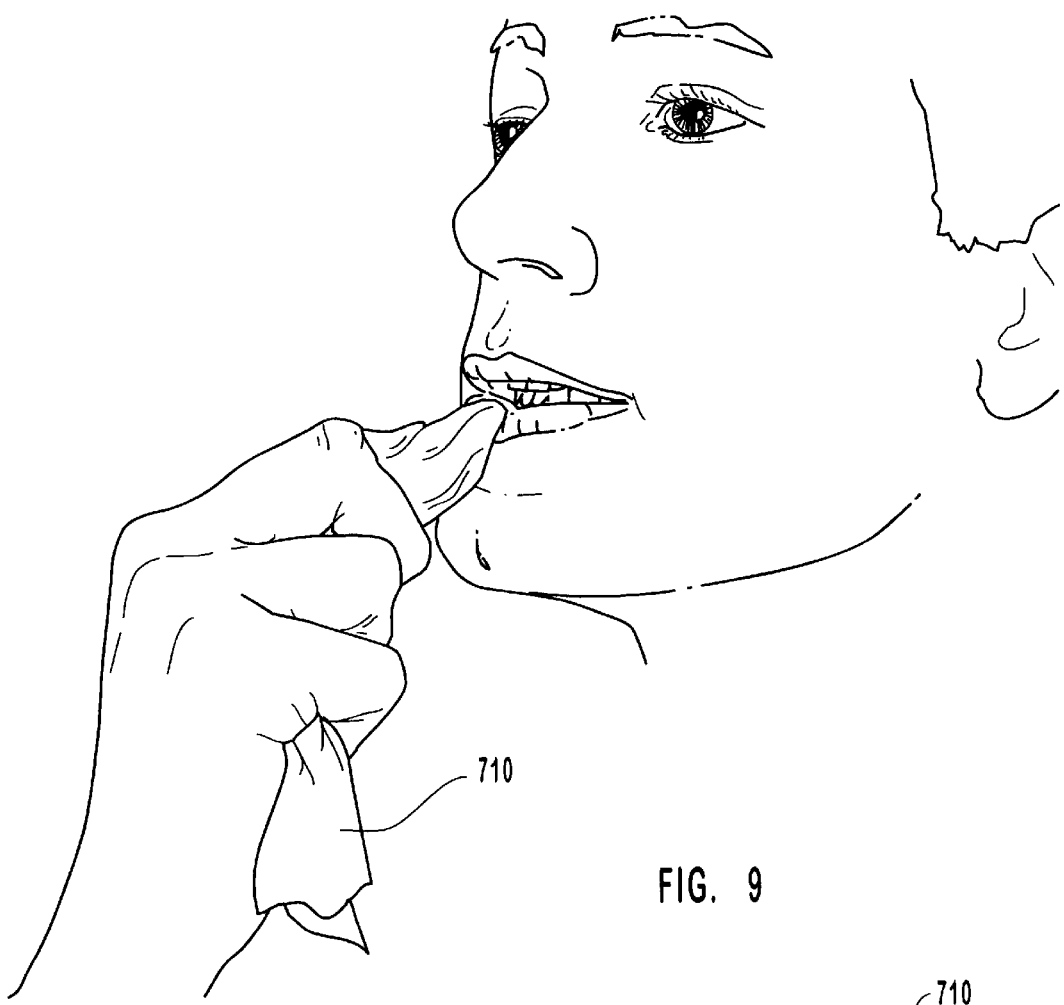
FIG. 9 is a perspective view of a towelette being used to apply the treatment composition to a cold sore.
Figure 10:
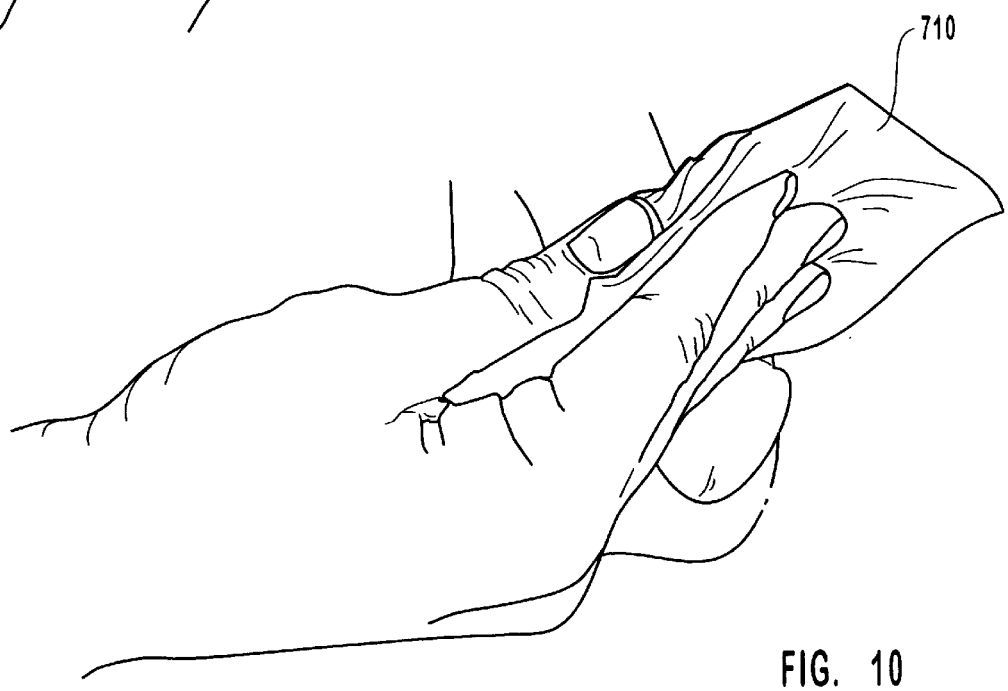
FIG. 10 is a perspective view of a towelette being used to apply the treatment composition to a sore on male genitalia.
Figure 11:
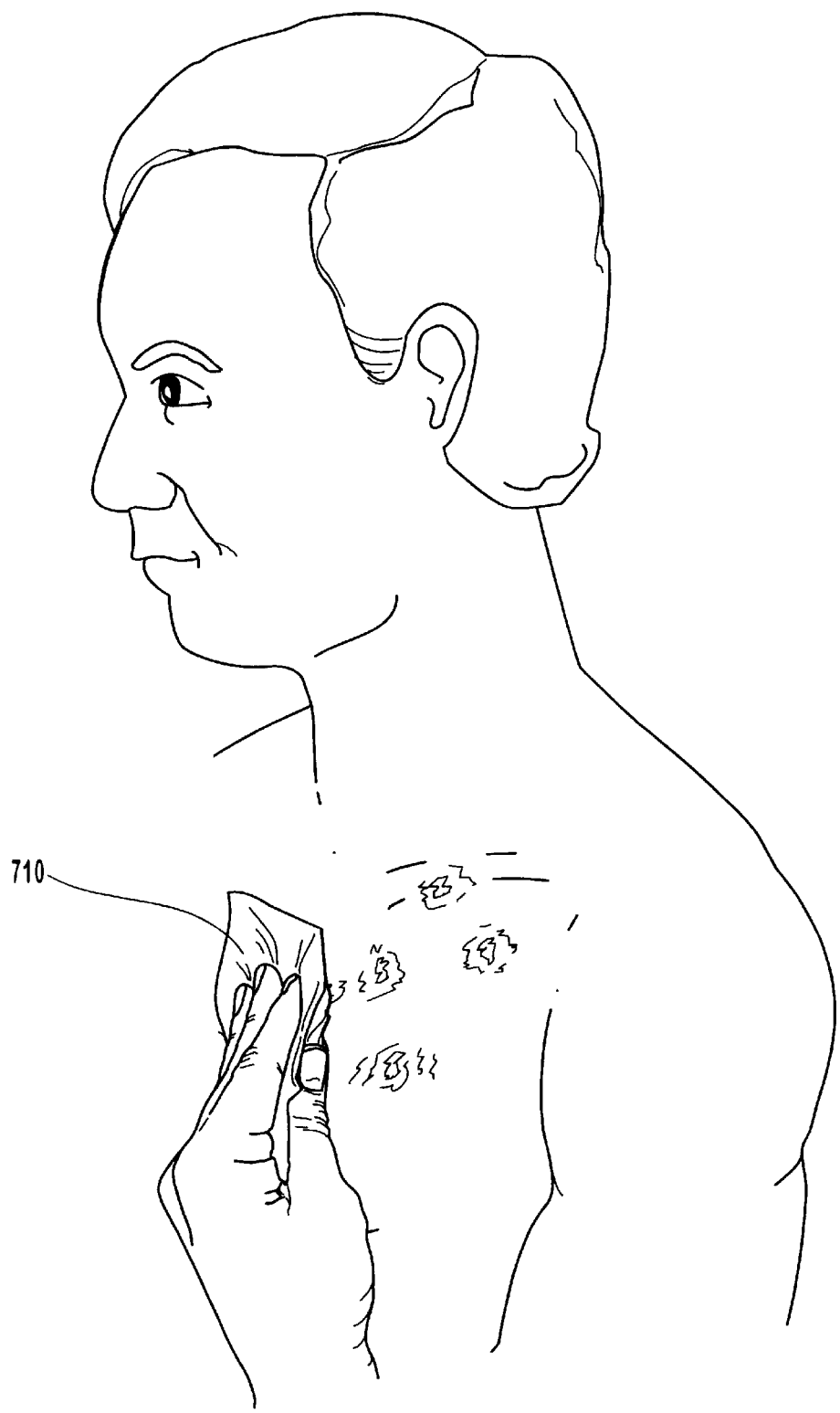
FIG. 11 is a perspective view of a towelette being used to apply the treatment composition to sores from shingles on the chest area.

Hereinbelow is a discussion of what is meant by vigorous irritation of disordered tissue, followed by a detailed description of the treatment composition. The description of the treatment composition is followed by a detailed description of several embodiments of applicators. FIGS. 2A–2F depict a preferred applicator. Other embodiments of applicators are shown in FIGS. 3–8. FIGS. 9–11 depict towelettes being used. FIG. 1 depicts a cross-sectional view of skin.

The phrase "vigorous agitation" means that the skin is irritated in a manner that allows the inventive compositions to penetrate below the surface of the skin, preferably to a nerve ending. As described in more detail hereinbelow, such vigorous agitation is achieved through either applying an appropriate amount of pressure for an adequate period of time and/or appropriate rubbing for an adequate period of time. Vigorous agitation is preferably a combination of both adequate pressure and rubbing.

A suggested theory for the effectiveness which results from vigorously agitating the disordered tissue is set forth below. However, it should be understood that the objective in vigorously agitating the disordered tissue includes moving the tissue to better enable the treatment composition to physically move through the layers of the disordered tissue by moving the cells and fluids in the disordered tissue. Also, another objective of vigorous agitation is to stimulate the immune responses.

Vigorous agitation achieved through applying appropriate pressure may be understood to be an amount of pressure such that, where tissue overlies bone, the tissue is depressed to be firmly against the bone. Similarly, if the disordered portion of the tissue is adjacent to teeth or gums such as the skin around the mouth, then the disordered tissue is sufficiently compressed due to the pressure that the pressure is felt on the opposing surfaces within the mouth. Additionally, if disordered tissue located around a patient's lip is also opposite the patient's gums then pressure applied to the disordered tissue would also be felt at the portion of the patient's gums opposite the disordered tissue through the lip or cheek.

Vigorous agitation achieved though rubbing involves repeated movement of the applicator in a frictional manner with the disordered tissue. For example, the applicator may be moved in a steady back and forth motion on the disordered tissue or rotated as the treatment composition is applied or after delivery of the composition. As described in greater detail in reference to the applicator, the applicator is preferably configured to provide a relatively uniform abrasive action. The oscillation rate of the back and forth motion depends on several factors such as the amount of pressure being simultaneously applied and the condition of the disordered tissue. So in some instances the oscillation rate may be only 1 stroke every few seconds while in other circumstances the oscillation rate may range from about 1 strokes per second to about 10 strokes per second. More typically, however, the oscillation rate is in a range from about 2 strokes per second to about 6 strokes per second and is most typically in a range from about 3 strokes per second to about 4 strokes per second Note that the portion of the applicator used to rub the disordered tissue preferably has a size in a range from about 50% to about 200% the size of the disordered tissue treatment site. For example, it has been found that a contact surface that is about 8 mm in diameter is useful for agitating most cold sore treatment sites.

The length of time that vigorous agitation of this type may be sustained upon a disordered tissue treatment site may vary according to the individual, the size of the s applicator surface in relation to the size of the disordered tissue to be agitated, the amount of pressure applied as defined above and the oscillation rate of the rubbing. As the length of time increases in which the applicator delivery surface is maintained in contact with the disordered tissue, the required pressure decreases for achieving the desired penetration of the treatment composition into the disordered tissue. Typically, the vigorous agitation is maintained for at least 1 second and is more typically maintained for a few seconds. However, the period of time may range from about 3 seconds to about 1 minute depending on the condition of the disordered tissue, the amount of pressure being applied and/or the movement of the applicator. Vigorous agitation is most typically maintained for a period of time in a range from about 5 seconds to about 15 seconds.

The intensity of the vigorous agitation is adjusted depending on the thickness of the skin. For example, the tissue on a lip that must be penetrated is much thinner than that of the skin on the arms, legs, and chest. The thickness is even greater for the skin on the palms of hands and feet and is still greater for other body parts such as backs. So it may be necessary to vigorously agitate the disordered tissue with greater intensity when treating sores on a patient's chest or back caused by shingles then the vigorous agitation is required to treat a cold sore on one's lip.

It is counterintuitive to vigorously agitate disordered tissue such as a cold sore as the disordered tissue already hurts so one inherently desires to avoid even contacting such sensitive disordered tissue. However, patients are likely to be more tolerant of any pain which may result from vigorous agitation when bolstered by knowledge that vigorous agitation significantly enhances the ability of the treatment compositions disclosed herein to effectively penetrate disordered tissue.

Vigorous agitation need not necessarily be painful, although, vigorous agitation may also be understood to mean that discomfort is felt by the patient beyond nominal dabbing of the disordered tissue as with other treatments that call for gentle application to the disordered tissue. Before a cold sore has erupted, and is in the prodromal stage or vesicular stage such that at most there is merely a vistule, it may not be painful to vigorously agitate the disordered tissue. However, when vigorously agitating disordered tissue which is in an erupted stage, the agitation may be sufficient to cause sharp pain and bleeding.

Obviously however disordered tissue such as cold sores cannot always be vigorously agitated. As indicated above, when a cold sore is in the prodromal stage it can be vigorously agitated without significant sensitivity. However, when the cold sore has become an open sore less pressure may be utilized so as to minimize the potential for causing pain. Also, if the cold sore has coalesced then it is best not to vigorously agitate the treatment site as such action is likely to disturb the coalesced tissue, scab, etc. Also, when treating sensitive areas such as inside the mouth, mucous coated tissues, the eyes, genitalia, etc. the treatment composition should be applied without vigorous agitation.

As indicated above, the vigorous agitation can also be defined by contrasting it with nominal dabbing of the disordered tissue which involves the mere application of a treatment composition. The same is likewise true for other application techniques such as swabbing, sponging, and brushing merely to ensure that a treatment composition is applied or delivered. Dabbing and other application techniques do not involve pressing hard enough such that the disordered tissue is compressed against a bone or such that pressure is felt as a surface in the mouth opposite the disordered tissue is pressed against teeth or gums. Mere application of a treatment composition such as nominal dabbing of the disordered tissue does not cause bleeding of the disordered tissue, for example, if it is a cold sore in an erupted stage.

Despite a patient's desire to enable disordered tissue to return to normal some patients are also likely to adjust the amount of pressure applied or the rate of rubbing in order to experience minimal pain. However, as indicated above, it is not necessary for a patient to feel pain in order for the treatment composition to be delivered with vigorous agitation. The objective is to move the tissue somehow either through compressing the tissue through the application of an appropriate amount of pressure as discussed above for an adequate period of time and/or by rubbing the tissue in manner such that tissue is moved around for an adequate period of time for the treatment composition to penetrate such that it does not remain on the surface.

The treatment composition is preferably absorbed into the disordered tissue to such an extent that within several minutes after application the composition can no longer be seen. This is absorption or penetration rate is achieved either with or without vigorous agitation. More preferably, the composition is not visibly detectable within 2 minutes after being applied and is most preferably not visibly detectable within 1 minute after being applied. Note that the content of the composition has different formulations, however, in the preferred embodiment there is no residue remaining after the composition has been applied and absorbed which is visibly detectable.

As indicated above, the treatment composition preferably penetrates through the skin to a nerve ending or causes a penetration sensation at the nerve ending. The pathway for this penetration is discussed in greater detail below with reference to FIG. 1. After the composition is delivered with simultaneous agitation, the penetration or the penetration sensation preferably occurs within about one minute. The penetration or penetration sensation to a nerve ending is more preferably achieved in about 30 seconds and most preferably in less than about 10 seconds. In more serious cases when the disordered tissue represents an extensive problem, several treatments may be used instead of a single, primary treatment. Note that when several treatments are used instead of a single, primary treatment, it is preferable to use a clean and sterile applicator for each repeated treatment.

FIG. 1 is a vertical cross-section of the epidermis and the papillae of the dermis. FIG. 1 illustrates the stratum corneum 28 disposed upon the fatty layer or stratum lucidum 30. The stratum lucidum is disposed over the stratum granulosum 32. Below the stratum granulosum 32 is the stratum spinosum 34. Typically, the stratum spinosum 34 has a lipid film disposed around each individual cell. Below the stratum spinosum 34 is the stratum basale 38 that overlies vascularized tissue. Within the vascularized tissue the nervous papilla of the corium 36 is located along with blood vessels and nerves 40. FIG. 1 shows the treatment composition being delivered to the stratum corneum 28 in order to allow treatment composition 22 to penetrate therethrough. The treatment composition is shown being delivered from an impregnated agitation pad 12 accompanied by vigorously rubbing.

The arrows illustrate directions of agitation movement by way of non-limiting example. Note, however, that FIG. 1 does not depict the application of pressure as the objective in FIG. 1 is to show the particular layers involved in their natural positions and once pressure is applied the layers are moved from their natural positions. Although the inventor does not wish to be bound to a single theory, it is postulated that treatment composition 22 may move through the stratum corneum 28 without significant rupture thereof due to the vigorous agitation by impregnated agitation pad 12. Treatment composition 22 can penetrate to the nervous papilla of the corium 36 by the combination of vigorous agitation and the penetrating nature of the carrier. Preferably, vigorous agitation and the combination of the penetrating quality of the carrier are sufficient conditions to cause the anti-infective active agent to penetrate the disordered tissue to a nerve ending such as the nervous papilla of the corium 36.

Note that the application of pressure further increases the ability of the treatment composition to penetrate as the pressure may flatten or compress the layers and may assist in forcing the treatment composition downward. In any event, under the inventive conditions, penetration to the nerve ending is rapidly accomplished, preferably in several seconds.

While the treatment composition 22 rapidly penetrates to the nerve endings, it is also postulated that the treatment composition resides in reservoir amounts within the stratum spinosum 34 and may continue to diffuse across the stratum basale 38 to the nerve endings over an extended period of time. Vigorous agitation may assist in displacing fluid held within the stratum spinosum which is then replaced with the treatment composition. When the stratum spinosum 34 is filled with the treatment composition then the treatment composition is available as a bath that continues to provide protection as it slowly diffuses. On this basis, it is preferred to deliver a large quantity of the treatment composition on the disordered tissue such that the stratum spinosum 34 is saturated in the region of the cold sore or other disordered tissue for a period that enables the treatment composition to achieve its purpose before it diffuses into the body. For example, the volume applied to a typical cold sore may be in range from about 0.2 ml to about 1 ml, preferably in range from about 0.4 ml to about 0.8 ml and is most preferably about 0.6 ml. Low amounts of volume, such as about 0.2 ml, work for a single cold sore especially if the applicator does not retain a significant portion of the volume however the volume is preferably greater. In order for all of the volume to be delivered, half of the total volume in the applicator may be delivered and then the remainder may be delivered. Delivery of such large volumes is discussed below in reference to the applicators used to deliver the treatment composition.

The treatment compositions include at least a biologically active agent and a carrier. The biologically active agent is able to be effective in stopping tissue disorders such as cold sores, as the carrier is selected to optimally enable the treatment composition to penetrate. The biologically active agents suitable for use in the treatment compositions are set forth hereinbelow and then the carriers are described. Other optional components are also described.

The biologically active agents or anti-infective agents included in the anti-infective treatment compositions are preferably anti-infective organohalides, especially anti-viral organohalides. Benzalkonium chloride is the preferred organohalide. However, other organohalides or quaternary ammonium compounds may be used as the active agents in the compositions. Other active agents that are organohalides may include organo-bromides and organo-iodides. Preferably, the organohalides have an alkyl group attached thereto such as a simple $C_nH_{2n+1}$ chain, where n is in a range from 1 to about 50.

The chemical structure of benzalkonium chloride is shown below:

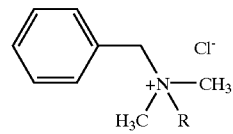

wherein R=$C_8H_{17}$ to $C_{18}H_{37}$. As shown, benzalkonium a benzene and a nitrogen constituent bound to the ring by a carbon atom. Two methyl groups and an R group of varying size extend from the nitrogen atom. Suitable benzalkonium chloride may be obtained from many suppliers for example, Spectrum of Gardena, Calif. Stephan of Northfield, Ill. Sanofit Pharmaceuticals, Inc. of New York, N.Y. and Mason Chemical of Arlington Heights, Ill.

These anti-infective agents, particularly benzalkonium chloride, are highly effective in limiting the source of infections and other complications related to disordered tissue. Also, these anti-infective agents destroy or eliminate toxins caused by substances such as viruses. Note that the toxins and their sources are rapidly eliminated to result in almost immediate pain relief While the active agents include organohalides, most suitable organohalides are organochlorides. Benzalkonium bromide is an example of a suitable organohalide which is not an organochloride. Benzalkonium bromide has the structure of benzalkonium chloride with the difference that the chlorine is substituted with a bromine radical. Another example of a suitable organohalide which is not an organochloride is cetyl trimethylammonium bromide.

Other organochlorides which have anti-infective properties and are suitable for use as the anti-infective organochloride in the treatment composition include: benzethonium chloride, methyl benzethonium chloride, cetyl pyridinium chloride, chloroxylenol, hexachlorophene, triclosan, chlorhexidine. Note that some of the above organochlorides are not suitable for all purposes. For example, benzethonium chloride cannot be used in a manner which would enable it to be ingested in a toxic quantity as it is potentially toxic if ingested. Similarly, the concentration of benzalkonium chloride must not be excessively high.

Additional examples of other organochlorides which may be suitable, more particularly quaternary ammonium chlorides having an alkyl with 6–18 carbons, include: alkylbenzyldimethylammonium chloride, alkyldimethyl/ethylbenzylammonium chloride, n-alkyldimethylbenzylammonium chloride, diisobutylphenoxyethoxyethyldimethylbenzylammonium chloride, n—($C_{12}C_{14}C_{16}$) alkyl dimethylbenzylammonium chloride, didecyldimethylammonium chloride, dioctyldimethylammonium chloride, dialkyldimethylammonium chloride, dialkylmethylbenzylammonium chloride, octyldecyldimethylammonium chloride, lauryldimethylbenzylammonium chloride, o-benzyl-p-chlorophenol, dideryldimethylammonium chloride, dioctyldimethylammonium chloride, alkyl ($C_{14}C_{12}C_{16}$) dimethylbenzylammonium chloride. In addition to these organochlorides, other known antimicrobial agents may also be used as the active agent or in combination with the active agents provided above. For example, chemicals which are known to act as an antiviral, antibacterial or antifingal agents such as the antifungal agents disclosed by Chodosh in U.S. Pat. No. 5,661,170 and U.S. Pat. No. 5,827,870, which are hereby incorporated by reference. It is also possible that a chemical such as acyclovir may be effective as an anti-infective agent when delivered with the carriers as disclosed herein combined with vigorous agitation. So in contrast to the conventional understanding that acyclovir is ineffective when topically applied, it may be useful as an anti-infective agent when used as taught herein. Note, however, that acyclovir is not an organohalide and so may not be as easily absorbed into the skin or penetrate as readily. However, to the extent that acyclovir, related substances such as denever, femiver or any other suitable anti-infective agent can be delivered in the inventive compositions or in accordance with inventive methodologies and systems, it is also within the scope of the present invention.

When the anti-infective agent is benzalkonium chloride, the concentration is preferably in a range from about 0.01% to about 0.5% by volume of the treatment composition, more preferably in a range from about 0.05% to about 0.3% by volume of the treatment composition, and even more preferably in a range from about 0.1% to about 0.2% by volume of the treatment composition. Concentrations above 0.5% by volume are considered to pose potential toxicity problems, accordingly, the concentration is preferably less than 0.26% and is most preferably about 0.13% by volume of the treatment composition. Depending on the particular, organohalide or quaternary ammonium chloride, the concentration may vary. For example, the concentration may range from about 0.001% to about 2% by volume of the treatment composition.

For the specialized treatment of the eyes, an eyewash having the active agent is made into a composition with an active agent concentration in the volume range from about 0.001% to about 0.05%. Preferably, the active agent concentration for an eyewash is in the range from about 0.005% to about 0.03%. Higher concentrations may be administered by a medical professional. The specialized treatment of the eyes may also require several treatments instead of a single, primary treatment. Where eye drops are used, according to the inventive method, the composition is deposited onto the eye and the patient closes the eye after the eye has been contacted with composition, and the patient may opt to rub the eyeball through the eyelid to assist in the delivery of the treatment composition and the penetration into the eye tissue. If the disordered tissue is in a corner of the eye, it may even be vigorously agitated. A subsequent treatment and a series of subsequent treatments may also be carried out on the eyes.

As indicated above, the carrier is a vehicle for the biologically active agent, more particularly the anti-infective active agent. The carrier causes effective wetting of the tissue to be treated and then enables the anti-infective agent to move within this carrier into the disordered tissue.

In one embodiment, the treatment composition consists of only the active agent such as benzalkonium chloride and the carrier. In other embodiments, the treatment composition consists essentially of the active agent and the carrier, however, other components may also be included as described hereinbelow. In any event, the carrier is preferably sufficiently inert with respect to the active agent and any other component present to enable the treatment composition to be stored for long periods of time without deactivating the anti-infective agent, such as a 1 year period and preferably a 2 year period.

The carrier has properties which enhance the ability of the treatment composition to penetrate into the disordered epithelial tissue. More particularly, the carrier has a viscosity and/or density which is not significantly greater than that of water in order to optimally enable the treatment composition to penetrate into the disordered tissue. Using a carrier having a viscosity which is not significantly greater than that of water is in sharp contrast to conventional compositions which enable the composition to be coated onto afflicted tissue. Accordingly, the treatment compositions specifically exclude formulations which may be considered to be primarily or essentially gels, creams, lotions, oils, ointments, pastes, emulsions, and colloidal suspensions. Note however that small amounts of inert abrasive material may be present in the treatment compositions as discussed hereinbelow. Note also the carrier may include substances which have either a viscosity or density which is more than slightly greater than that of water as long as other substances are also included in the carrier such that the mixture has either a viscosity or density which is not significantly greater than that of water.

The carrier preferably has a tissue penetrating component such as isopropyl alcohol that is capable of penetrating the skin in a rapid manner without rapidly diffusing beyond the skin into the body. More particularly, the carrier preferably enables the stratum spinosum to be saturated in the region of the cold sore or other disordered tissue for a period that enables the treatment composition to achieve its purpose before it diffuses into the body.

The carrier may be formed from a single liquid constituent such as isopropyl alcohol or water as described hereinbelow, or from more than one constituent. Although, water alone may be used as the carrier, it is not preferred because other compounds, such as some alcohols, have a tissue penetrating capability that water does not have. The carrier in the treatment composition is also preferably not formed entirely from an alcohol such as isopropyl alcohol or ethyl alcohol, since their use may be more painful in some circumstances. More particularly, when an open sore is part of the disordered tissue, the amount of alcohol or other composition that has a significant tissue penetrating ability may be modified by adding water so as to moderate the amount of discomfort that the patient experiences by the application of the composition to the open sore. Additionally, the evaporation rate of a carrier that includes alcohols such as isopropyl alcohol can be reduced by including water. Further, it may be preferred to use alcohols such as isopropyl alcohol with other constituents such as water due to regulatory issues. Also some substances, such as benzylkonium chloride, dissolve best in a carrier that includes water.

While isopropyl alcohol is a preferred carrier due to its ability to effectively penetrating tissue, other alcohols may also be used. In addition to isopropyl alcohol, ethanol, and methanol are also suitable carriers. Benzyl alcohol can be used as a carrier or as an additive as it also acts as a bacteriostat and an anesthetic. Mixtures of the above-mentioned alcohols are also preferred depending upon the application. As indicated above, however, isopropyl alcohol or ethyl alcohol is preferably used in combination with other carrier constituents. For example, as mentioned above water may be added to isopropyl alcohol to reduce the pain which may be felt when only isopropyl alcohol is used. Similarly, isopropyl alcohol may be utilized with cetyl alcohol or with a combination of both cetyl alcohol and water to reduce the sensation.

As noted above, the carrier preferably has a tissue-penetrating constituent such as isopropyl alcohol. It has been noted that the ability of the treatment composition to penetrate disordered tissue is significantly enhanced when at least a portion of the carrier is isopropyl alcohol. While not being limited by any particularly theory, it is suggested that isopropyl alcohol opens cells and is not blocked by lipids or lipid layers in the disordered tissue. Accordingly, it is believed that isopropyl alcohol penetrates so effectively due to its ability to remove lipids from the tissue. The penetration ability of a carrier comprising isopropyl alcohol may be further enhanced by including a very small amount of ethyl alcohol such that the carrier is less than about 1% ethyl alcohol.

As indicated above, the preferred carrier includes isopropyl alcohol and water. As also discussed above, isopropyl alcohol is included in the carrier for its ability to rapidly penetrate disordered tissue while the water is included primarily to minimize the sensation which may be felt as the isopropyl alcohol penetrates the skin. While substances like lidocaine and other substances that have anesthetic qualities can be used instead of water to reduce the sensation caused by isopropyl alcohol, the carrier preferably includes water with the isopropyl alcohol as benzalkonium chloride dissolves more easily in such a combination than in isopropyl alcohol alone. It is also simpler to use a carrier that includes both isopropyl alcohol and water than it is to pretreat the disordered tissue with an anesthetic composition. However, pretreating the disordered tissue with an anesthetic composition is also within the scope of the present invention.

Carriers that include isopropyl alcohol and water have varying ratios depending on the intended use. However, for titating cold sores the water is preferably included in a range from about 10% to about 50% by volume of the carrier with the remainder being isopropyl alcohol. The water content is more preferably in a range from about 20% to about 40% by volume of the carrier. The most preferred carrier for treating cold sores is a carrier wherein water is included in an amount of about 30% by volume of the carrier and wherein the isopropyl alcohol is included in an amount of about 70%. Although, these ranges of water content are provided based on the volume of water in the carrier, essentially the same water contents apply to the overall treatment composition since the other active agent and any other optional component are typically included in such small amounts. For example, the most preferred composition is a treatment composition including about 0.0133% benzalkonium chloride by volume of the treatment composition, 29.987% water by volume of the treatment composition and 70% isopropyl alcohol by volume of the treatment composition.

When treating sensitive parts of the body such as the genitalia and adjacent areas, the carrier may include isopropyl alcohol in an amount of about 10 to about 15% by volume of the carrier and water in an amount of about 85% to about 90%. However, as noted above, higher concentrations can still be used even in sensitive areas, particularly when pretreated with an anesthetic composition.

While rapid penetration is desired, it should be understood that the objective is rapid penetration to the nerve ending without thereafter rapidly passing through the skin and into the blood stream Accordingly, the carrier preferably does not include substances or at least not large quantities of substances such as dimethyl sulfoxide (DMSO) as such substances immediately penetrate the skin and enter the blood stream.

The carrier may also include acetic compounds such as acetone, acetic acid, acetic anhydride, and the like. However, if acetone and the like are used they are preferably used in small quantities and not as the sole constituent as they evaporate to rapidly and do not penetrate as well as isopropyl alcohol. While some acetic compounds may not be as effective as certain alcohols, particularly isopropyl alcohol, acetone does exhibit some ability to penetrate tissue. So although acetic compounds such as acetone may be used alone it is preferably used in combination with other substances. One preferred carrier combination is ethanol and acetone in a ratio of about 70% ethanol by volume of the carrier, preferably 80% ethanol and most preferably about 90% ethanol with 10% acetone by volume of the carrier. As mentioned above with respect to the water content for carriers formed from water and alcohol, the ratios provided for combinations of ethanol and acetone based on the volume of the carrier apply also to the volume of the treatment composition.

The above carriers may also be combined across class lines. As such, the carriers such as water, alcohols, and acetic compounds may be combined. One example is water, alcohol, and acetone in respective amounts of 30%, 60%, and 10%, by volume of the carrier. Generally speaking, the constituents may be combined in any suitable ratio such as: 1:1:0, 1:2:0, 1:10:0, 1:1:1, 1:2:1, 1:10:1, 1:10:10, and 1:2:10.

As indicated above, the carrier is preferably a liquid that includes alcohol as it is believed that alcohols included in sufficient quantity to act as the carrier may have the quality of removing lipids from the tissue and thereby enabling the active agent to move within the disordered tissue. It is also believed that the ability of the treatment composition to penetrate the disordered tissue is hindered by including components in the composition such as oils or materials which have traditionally been included to enable the composition to be coated onto the surface of the disordered tissue. Examples of such materials include petrolatum which is used in various cold sore treatment compositions. For example, the popular over-the-counter lip ointment sold under the trademark BLISTEX by Blistex Incorporated of Oakbrook, Ill. 60521. The BLISTEX-ointment contains allantoin (1%), camphor (0.5%) and phenol (0.5%) in an emollient base with petrolatum, lanolin, menthol, methyl salicylate, and other ingredients. Other widely used ingredients which are included to increase the viscosity or to increase the tackiness includes polyethylene glycol and polypropylene glycol. An example of a product which utilizes polyethylene glycol and polypropylene glycol is a gel sold under the trademark ORAGEL MOUTH AID by Del Laboratories Incorporated of Farmingdale, N.Y. 11735. Other thickeners are taught in U.S. Pat. No. 5,661,170, which was previously incorporated by reference, as including cellulosic materials and waxes. In addition to petrolatum based materials and thickeners, it is also believed that materials which are either obtained from natural sources such as naturally occurring oils present in trees, bushes, plants, etc. or substances which are derived from such oils may also reduce the ability of the treatment composition to penetrate the disordered tissue. Such materials are referred to herein as penetration inhibiting components.

As indicated above, penetration inhibiting components include chemicals which are petrolatum based substances, materials conventionally utilized as thickeners, naturally occurring oils, substances derived from naturally occuring oils or any other substance which is added primarily to increase the tendency of a treatment composition to remain on the surface of disordered tissue such as a cold sore. Note that while substances such as petrolatum or thickeners are not added individually, a component may be added which includes minute amounts of naturally occuring oils or substances derived from oils obtained from natural sources. So although, the inventive composition is preferably substantially oil free, the term "substantially oil free," is meant that oil substances are preferably not individually added, but may be present due to the natural content of a substance added to the inventive composition. As such, it may be incidentally present in a amount of less than about 2% by volume, and is preferably incidentally present in an amount of less than about 0.1%, and is most preferably incidentally present in an amount less than about 0.02% and even more so at m amount less than about 0.01%. Additionally, in some instances it may be desirable to add very small quantities of naturally occuring oils or substances, however, the concentration is no more than the incidental amounts discussed above.

Note that penetration inhibiting components, are believed to act as a barrier which seals in toxic irritating by-products of viral growth. They prevent the natural weeping process of the disordered tissue which flows to remove toxins, etc. Accordingly, use of such penetration inhibiting components causes more damage to the disordered tissue despite the temporary advantages achieved though using such substances.

As indicated above, the treatment composition may consist of only the active agent and the carrier. Treatment compositions consisting essentially of the active agent and the carrier do not include penetration inhibiting substances but may include other components added for specific purposes. These components or additives are added to achieve a particular result and do not have a substantial impact on the ability of the treatment composition to penetrate into the disordered tissue or the ability of the treatment composition to be anti-infective. Examples of such components are additives which are conventionally used as preservatives, pH adjusters, substances having anesthetic qualities, vasodilators, analgesics and defoamers. These components or additives are used in concentrations which correspond with amounts conventionally utilized.

Generally, preservatives may be added to the anti-infective composition. Examples of preferred preservatives include parabens, preferably the methyl and propyl parabens. Preferably the preservatives, if present, are supplied to the composition in a range from about 0.0001% to about 0.01% by volume of the treatment composition.

Additives such as those set forth above can be blended with other ingredients to make up the inventive composition including pH adjustors. Such pH adjustors may include organic acids, mineral acids in minute amounts, organic bases or mineral bases also in minute amounts. Preferred organic acids include citric acid, ascorbic acid, sorbic acid, malic acid, ascetic acid, succinic acid, caproic acid, and the like. Other preferred acids include hydrochloric acid, nitric acid, hydroiodic acid, and the like in minute amounts. Preferred bases include methyl and ethylamines such as triethanolamine, and the like. Other preferred bases include, ammonium hydroxide, potassium hydroxide, sodium hydroxide, and the like.

The inventive compositions may include compounds with anesthetic qualities. Depending upon the application site, whether on dermal layers or on mucous membranes, different anesthetics may be preferred. One particularly preferred anesthetic is benzocaine. Benzocaine is especially useful in the areas of open sores such as cold sores, eczema sores, and the like. Of the amides, such compounds as bupivocaine, carbocaine, and ropivocaine may be preferred. Of the esters, such compounds as procaine, cocaine, novocaine tetracaine and benzocaine may be preferred. Other preferred anesthetics include alkaloids such as cocaine, caffeine, nicotine, xylocaine, and the like. Another preferred anesthetic includes a combination of lidocaine and prilocaine. With these two compounds, an eutectic mixture is achieved with a melting point below room temperature. A preferred composition of the lidocaine and prilocaine is about 2.5% each in a 1:1 mixture. Other preferred anesthetics include oil of cloves, tea tree oil (melaleuca alternifolia, which also acts as a disinfectant) and the like. Other preferred anesthetics include lidocaine hydrochloride, dibucaine, dibucaine hydrochloride, tetracaine hydrochloride, tronothane, dyclonine, dyclonine hydrochloride, pramoxine hydrochloride, diperodon, butamben picrate, cyclomethycaine sulfate, cyclomethycaine hydrochloride, and dimethisoquin hydrochloride. Where an anesthetic is present, it is supplied to make up the composition in a range from about 0.001% to about 0.01% by volume of the treatment composition.

Other preferred components for the inventive composition include vasodilators such as nitroglycerine and the like. Vasodilators are useful for causing penetration of the active agent or agents into the disordered tissue to its base in the skin or mucous membranes an beyond. Care must be taken to balance the effect of localized vasodilation against the systemic toxicity of the inventive composition such that penetration into the disordered tissue is clinically significant, but that the active agent or agents remain substantially local to the disordered tissue for maximum efficacy. Where a vasodilator is supplied to make up the inventive composition, it may be provided in a preferred range from about 0.001% to about 0.05% by volume of the treatment composition.

Other preferred components for the inventive composition include analgesics such as methyl salicylate, aspirin, and other salicylate salts. Other preferred components for their analgesic effects include N,N-dimethyl aspartic acid, N-N-dimethyl glutamic acid, trolamine salicylate, antipyrine, and salicylamide. Where an analgesic is present, it may be supplied to make up the composition in a preferred range from about 0.001% to about 0.01% by volume of the treatment composition.

Most of the active agents disclosed above are considered to be cationic surfactants so it is generally unnecessary to include any surfactants. It is also generally unnecessary to include surfactants as the treatment composition is substantially oil free. Additionally, the active agent can be used with various carriers so the carrier can be modified to achieve optimal solubility as needed. To the extent that a surfactant is included, for example, to assist in tissue wetting properties, the surfactants may be anionic, cationic, or nonionic, and amphoteric. In some circumstances it may be useful to use other surfactants such as: another cationic surfactant, an ampholytic surfactant or a zwitterionic surfactant. U.S. Pat. No. 5,661,170, referenced above, may be referred to for a disclosure of suitable surfactants.

Abrasives are generally not necessary as a component of the composition as the applicators are configured for abrasion. Additionally, when irritating an open sore it would be undesirable for abrasives to be deposited into the open sore. Nor is it generally necessary to include abrasives on the applicators, which also risks the abrasives being dislodged from the applicator and into an open sore. However, this does not exclude the use of abrasives as free-floating inert components in a treatment composition nor their surface attachment to or impregnation in an applicator. If used, suitable abrasives may include pumice and the like as well as oxides such as alumina, silica, mica, zirconia, titania (both anatase and rutile), and the like.

In making a mixture of any of the preceding carriers and additives, it is understood that the recitation of compounds as mixtures includes the solution and reaction products thereof. A preferred method for preparing the inventive composition is to dissolve the anti-infective active agent into the carrier, such as to dissolve benzalkonium chloride in isopropyl alcohol In general, it is only necessary to mix the agent, such as benzalkonium chloride, into the carrier. In some instances, it may be helpful to first lower the pH of the solution into a range preferred to assist the dissolution of selected components. Note that benzalkonium chloride is alkaline. Following dissolution of the selected components that are assisted in their dissolution by a lower pH, the solution may be either warmed or the pH increased, or both, and other components may be added, preceding or following the warming and/or the pH increase.

The use of soap is preferably avoided in the inventive method as it tends to significantly reduce the efficacy of the methodology. However, the inventive method may include a precleaning step that comprises washing the disordered tissue treatment site. The precleaning step may include the use of a pre-moistened, organohalide impregnated towelette. Commercially available towelettes are preferably not used as these towelettes contain components which are generally considered undesirable in combination with the present invention. Accordingly, when a precleaning towelette is used, it is preferred that the towelette be moistened with a composition which does not contain any penetration inhibiting components such as lanolin. An example of a commercially available towelette is the PDI® towelette made by Professional Disposables, Inc. of Orangeburg, N.Y. which is impregnated with benzalkonium chloride. Another example is the WET ONES® towelette made by Playtex Products, Inc. of Dover, Del. which is pre-moistened, benzethonium chloride impregnated towelette.

In one method of the present invention, a topical anesthetic may be applied to the treatment site and enough time may be allowed to elapse in order to substantially anesthetize the nerve endings for disordered tissue and surrounding tissue at and near the treatment site. For example, towelettes may also be used that are impregnated with anesthetics to reduce the sensitivity of an area that is to be treated with vigorous agitation. After sufficient anesthetization of the treatment site, the inventive method continues by providing the inventive composition that contains the anti-infective agent followed by impregnating an applicator with the composition, or using a pre-impregnated applicator. Finally, the disordered tissue at the treatment site is vigorously agitated with the applicator while contacting the disordered tissue with the composition. According to this alternative inventive method, where a patient may have a low threshold of pain tolerance, the preliminary anesthetization of disordered tissue at and near the treatment site allows for the vigorous irritation of the disordered tissue without the accompanying discomfort.

Another alternative includes the application of a substance in liquid form in order to provide both sterile and cosmetic covering of the disordered tissue after the inventive vigorous agitation treatment. One example of a suitable liquid is NEW-SKINS® Liquid Bandage made by Medtech Laboratories, Inc. of Jackson, Wyo.

Applicators are preferably part of the inventive method and system. As such, applicators may be preconfigured with particular mixtures to treat specific disorders such as cold sores, eczema, and the like. Applicators are well known in the art. Examples thereof include those taught by Booras et al. in U.S. Pat. No. 5,709,866; by Fox in U.S. Pat. No. 5,704,906; by Mythling in U.S. Pat. No. 5,527,534; by Stalcup et al. in U.S. Pat. No. 5,016,651; by Bedford in U.S. Pat. No. 4,887,994; and by Korteweg in U.S. Pat. No. 4,952,204; the disclosures of which are incorporated herein by specific reference. Preferred applicators include prepackaged applicators that have agitation pads impregnated with the inventive composition. An applicator may be provided as a unitary structure such as a sealed container that is frangible and configured for a single use.

Applicators are preferably configured to enable the treatment composition to be either delivered with vigorous agitation or to be merely delivered onto the disordered tissue. Such flexibility is use ful since tissue disorders such as cold sores typically progresses in stages that have varying pain thresholds. whether the applicator is designed to vigorously agitate the disordered tissue or not, the applicator is preferably able to deliver large volumes of the treatment composition onto the disordered tissue. The delivery of large volumes of the treatment conposition may be achieved in several different ways. Applicators are also disclosed, however, that can only hold relatively small quantities of the treatment composition.

Figure 2A:
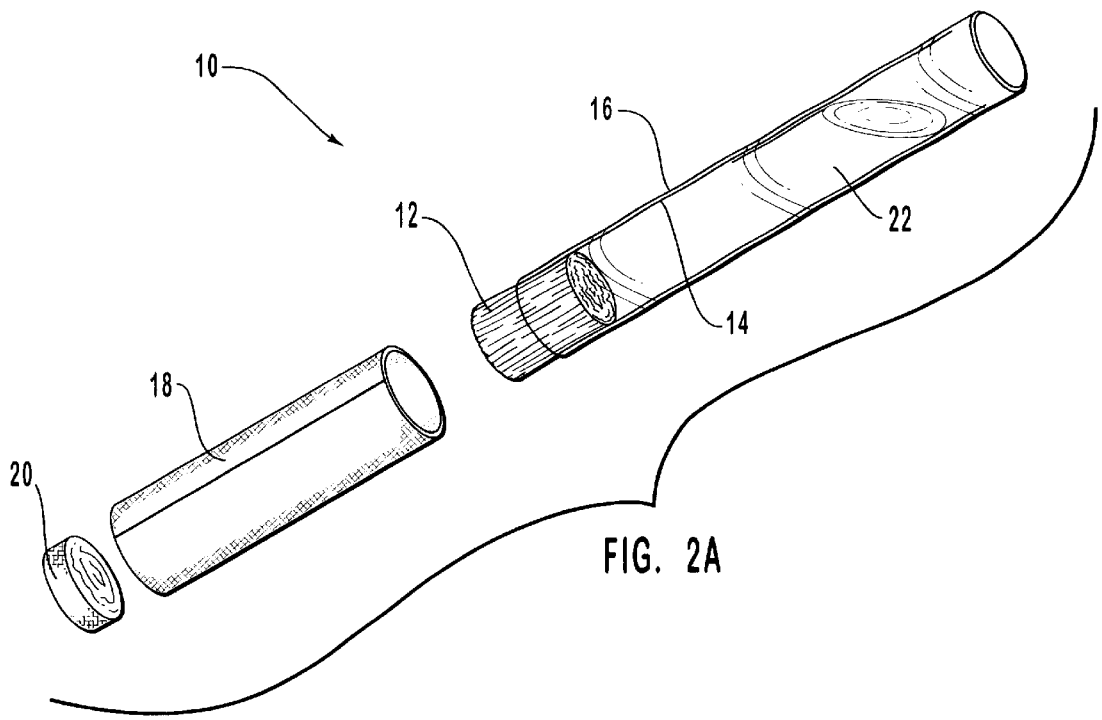
FIG. 2A is an exploded perspective view of a preferred applicator that contains the treatment composition.

FIGS. 2A–2E depict a preferred applicator 10. The details of applicator 10 are best seen in FIG. 2A which is an exploded perspective view, FIG. 2B a perspective view of the assembled applicator and FIG. 2C as it appears when ready for application.

Applicator 10 includes an absorbent, agitation pad 12, that is abutted against a frangible ampule or reservoir 14 via open delivery end 17 of the flexible container 16. Frangible reservoir 14 is housed in a container 16 that forms a holder for agitation pad 12. Frangible reservoir is enclosed by agitation pad 12, the sidewalls of container 16 and the closed end 19 of container 16. Frangible reservoir 14 is preferably a thin glass ampule while container 16 is preferably formed from a flexible plastic. A protective sleeve 18 is provided that is designed to keep agitation pad 12 free from contamination until applicator 10 is ready for use on the disordered tissue. A cap 20 is provided to fit into sleeve 18. The treatment composition 22 is held in frangible reservoir 14 until such time as frangible reservoir 14 is to be broken. One source for applicators having a frangible reservoir and various pad configurations is James Alexander Corporation of Blairtown, N.J.

Figure 2B:
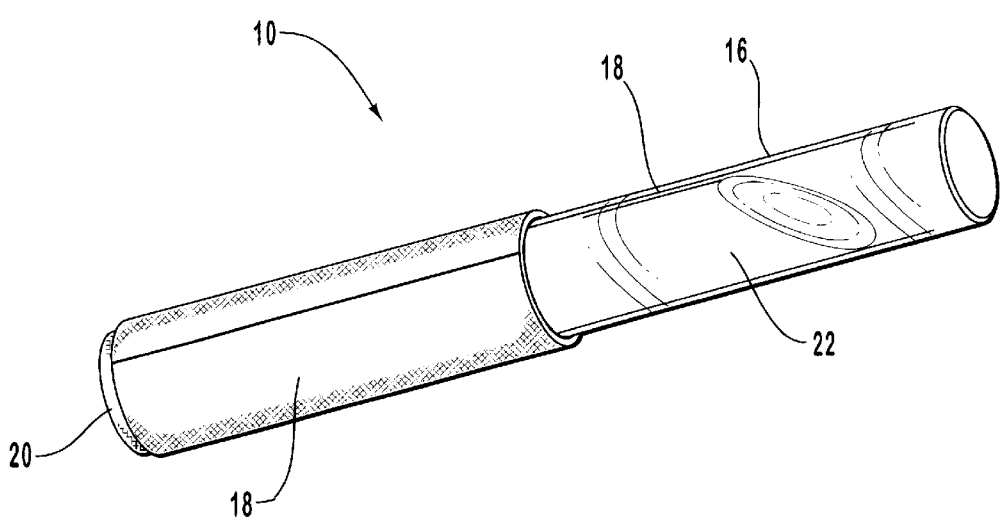
FIG. 2B is a perspective view of the preferred applicator depicted in FIG. 2A as it appears assembled prior to use.
Figures 2C, 2D:
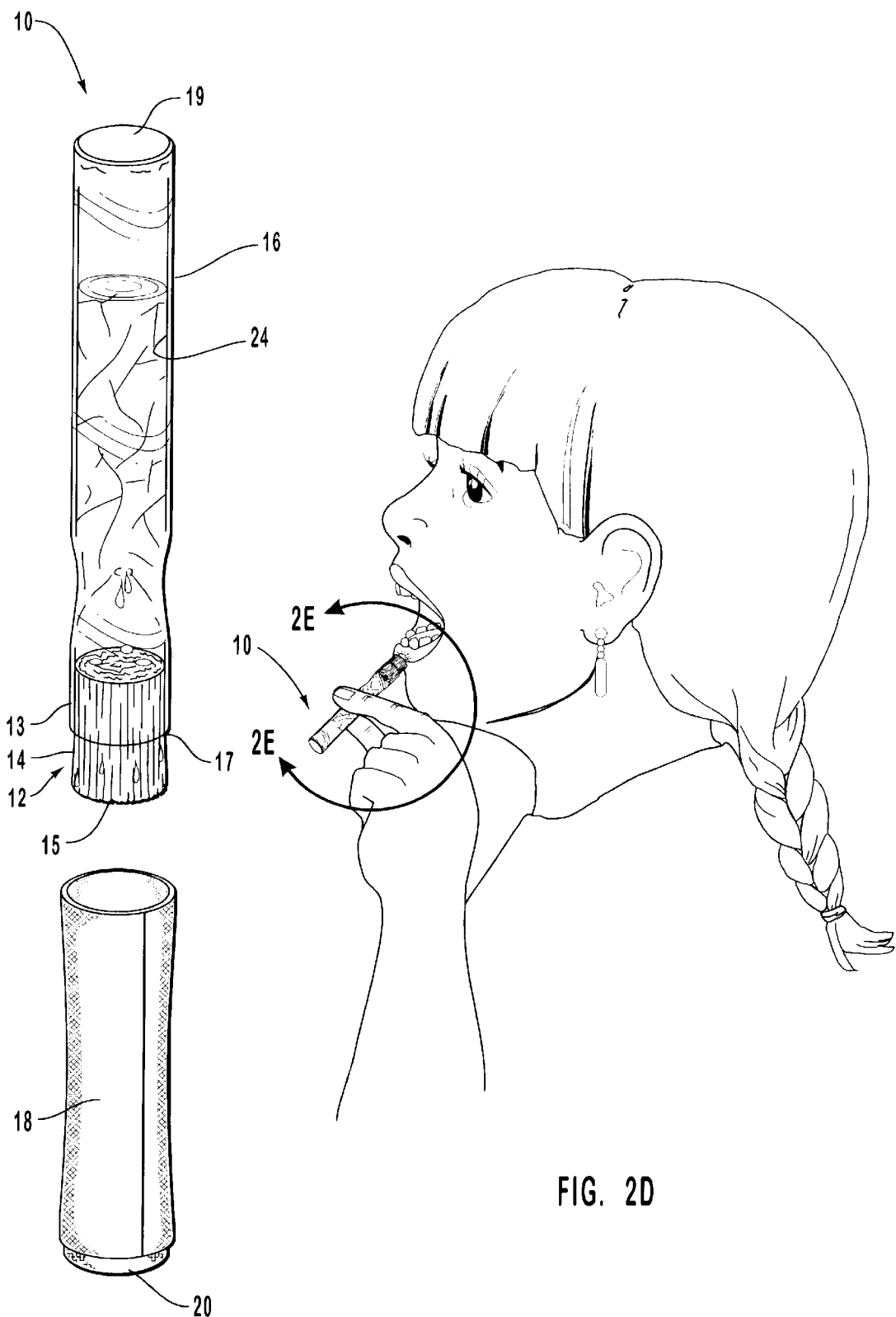
FIG. 2C is a perspective view of the preferred applicator depicted in FIG. 2B after the glass reservoir is crushed and the treatment composition is allowed to permeate the agitation pad.
FIG. 2D is a perspective view of an individual applying the treatment composition according to the present invention.

FIG. 2C is a perspective view of the preferred applicator depicted in FIG. 2B after frangible reservoir 14 has been ruptured. Treatment composition 22 is allowed to permeate agitation pad 12 in preparation for vigorous application to a disordered tissue treatment site. In FIG. 2C, sleeve 18 has been removed to expose an impregnated agitation pad 12. After impregnated agitation pad 12 is sufficiently wetted, application to the disordered tissue treatment site may commence.

FIG. 2D is a perspective view of an individual 26 applying treatment composition 22 to a cold sore at or near the lip according to the present invention. FIG. 2D illustrates that sufficient pressure is being applied against a non-puckered lip as the lip is pressed against the patient's teeth and/or gums in order to direct focused pressure into the disordered tissue while the active compounds are expressed from impregnated agitation pad 12 and into the disordered tissue. The combined effect of vigorous irritation of the disordered tissue and the administration of treatment composition 22 has the result of surprising therapeutic effects.

Figure 2E:
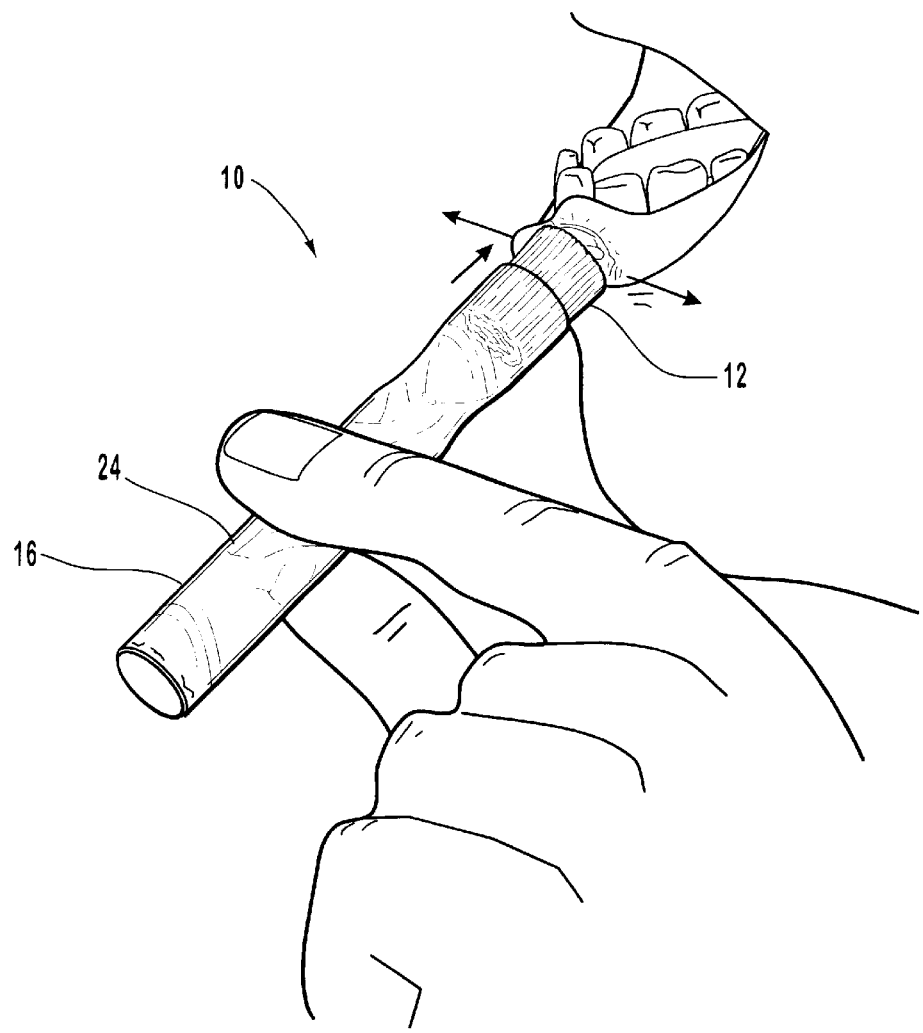
FIG. 2E is a detail taken along the section line 5—5 that depicts a close-up view of the inventive method.

FIG. 2E is a detail taken along the section line 2E—2E in FIG. 2D that depicts a close-up view of the inventive method. The detail view more clearly illustrates vigorous agitation of the disordered tissue site where impregnated agitation pad 12 is being pressed into the lip in order to be firmly felt at the gums or teeth opposite the disordered tissue. The arrows illustrate directions of agitation movement by way of non-limiting example.

Pad 12 has several purposes. Once frangible reservoir 14 is ruptured the treatment composition is delivered to pad 12 as gravity enables it to flow into pad 12, however, rupturing frangible reservoir 14 creates shards of glass. Pad 12 prevents these shards from passing and causing injury as the pad is used to deliver the composition to the disordered tissue. Another purpose of pad 12 is obviously the delivery of the treatment composition so the pad has a certain mesh or configuration that enables it to hold and deliver the treatment composition due to either porosity, capillary action, etc. As discussed above in reference to FIG. 2D, as pad 12 delivers the treatment composition it is also preferably used to vigorously agitate the disordered tissue.

Many configurations are available for a pad such as those disclosed in U.S. Pat. No. 1,822,566 and French Patent No. 2,700,698. The pad must of course be configured to prevent the passage of shards of glass out of container 16 and to enable treatment composition 22 to be held and delivered. The pad also preferably is configured for vigorously agitating the disordered tissue. Features that enable pad 12 to be used in vigorously agitating the disordered tissue are discussed below.

Figure 2F:
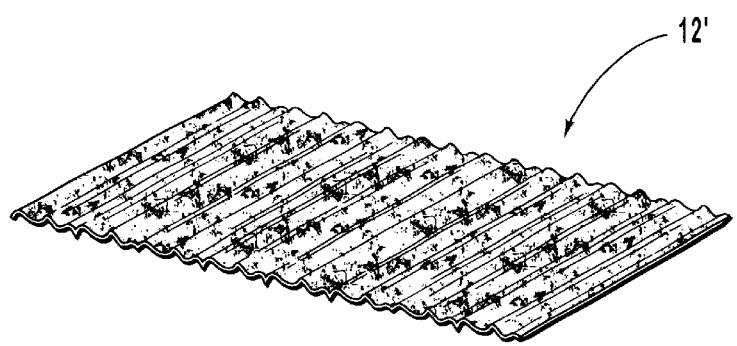
FIG. 2F schematically shows an embodiment of a pad that can be used to apply the treatment composition according to this invention.

Pad 12 is a folded sheet formed from a web of fibers. FIG. 2F depicts sheet 12' before it has been folded or collapsed to form pad 12. As shown in FIG. 2F, the sheet has a fluted appearance in order to provide an alignment such that when the sheet is gathered together in a bundle, it has longitudinal flutes. These longitudinal flutes provide a flow path for treatment composition 22 while the interlocked web of fibers prevents the shards of glass from passing out of container 16. Pad 12 has a configuration that is similar or identical to that of a cigarette filter. Examples of cigarette filters configurations that may be utilized are disclosed in U.S. Pat. Nos. 5,465,739 and 5,998,500, both of which are hereby incorporated by reference.

Pad 12 is preferably made of synthetic fibers that have a mesh which enables it to hold treatment composition 22 while having sufficient roughness to allow vigorous or continual agitation of the disordered tissue to enhance penetration by treatment composition 22. The fibers forming pad 12 are relatively densely positioned and are also relatively rigid. The dense positioning and the rigid nature of the fibers enables applicator 10 to be used to vigorously agitate the disordered tissue. Note that applicator 10 is not used like a brush to merely apply the treatment composition like conventional methodologies which involve coating the afflicted tissue. If the fibers are relatively soft such that they flex significantly when pushed against the disordered tissue then it is necessary to also push relatively hard against the disordered tissue in order to insure that the disordered tissue has been adequately agitated. Accordingly, the fibers are preferably relatively rigid through either proper selection of the fiber material, the length of the fibers and/or the positioning of the fibers.

Pad 12 has a retention portion 13 positioned within flexible container 16. Retention portion 16 is preferably attached to flexible container 16 through use of an appropriate adhesive that remains inert in the presence of the treatment composition or through heat fusing retention portion 13 and flexible container 16 together. Pad 12 also has a delivery portion 14 opposite from retention portion 16 that extends beyond open delivery end 17 of the flexible container 16. Regardless of the configuration of pad 12 or the material from which it is formed, the delivery portion is adapted to deliver the treatment composition to the disordered tissue while vigorously agitating the disordered tissue to enhance penetration of the treatment composition into the disordered tissue such that the treatment composition is no longer visibly detectable on the disordered tissue within several minutes after delivery of the treatment composition onto the disordered tissue.

Delivery portion 17 terminates at an agitation surface 15 that is relatively flat such that the disordered tissue is uniformly contacted. Uniformly contacting the disordered tissue with the flat surface reduces the risk of injuring the disordered tissue as the disordered tissue is vigorously agitated. Use of such a pad is to be contrasted with the use of a pad having a delivery portion that is bulbous such as a swab used in some applicators having a frangible ampule as disclosed in U.S. Pat. No. 1,822,566 and French Patent No. 2,700,698. A bulbous swab may tend to provide either insufficient contact when lightly pressed or uneven pressure when pushed hard enough to vigorously agitate the disordered tissue. Although use of such a bulbous swab in place of a pad such as pad 12 may result in these disadvantages, such swabs may be used in certain circumstances.

The fibers used in pad 12 are preferably formed from polyester as such polyester fibers provide adequate stiffness at the desired length. Pad 12 may also be formed from polyolefin, porous polyethylene or a laminated polyester fodm. As used in the specification and the appended claims, the term "fibers" includes both synthetic fibers, inorganic fibers, naturally occurring organic fibers and treated organic fibers. As indicated above, synthetic fibers such as polyester fibers are preferred. Another example of synthetic fibers includes polyethylene fibers. Polyethylene fibers having the same length and diameter as polyester fibers are not as preferred as they tend be softer. Of course the abrasiveness of fibers can be increased by increasing the diameter of the fiber; however, it is preferred not to increase the diameter of the fibers as this results in a decrease in surface area for the treatment composition to move downward on the fibers. Examples of inorganic fibers include glass, silica, ceramic, graphite, metal fibers, and mixtures thereof. Any fiber which has the preferred physical qualities such as strength, roughness, ability to hold liquids, and/or proper flexibility is also within the scope of the present invention. The only limiting criteria is that the fibers be able to be configured in a manner that enables them to hold the treatment composition and agitate the afflicted tissue without adversely reacting with the chemical constituents of treatment composition 22. Examples of naturally occurring fibers, include cellulosic fibers extracted from abaca, bagasse, hemp, cotton, plant leaves, wood or stems. The wood fibers may be both hard wood or soft wood, such as southern pine. While pad 12 may be made of such organic or naturally occurring fibers, it may be necessary to treat some naturally occurring fibers as discussed hereinbelow.

The retention portion of the pad has a length that is sufficient for the pad to be securely anchored in the open delivery end of the container. The delivery portion has a length and sufficient rigidity to enable the agitation surface to scrub the disordered tissue. When the pad is formed by folding or compressing together a sheet that is a polyester fiber web as shown in FIG. 2F at 12', the retention portion preferably has a length ranging from about 5 mm to about 7 mm and the delivery portion preferably has a length ranging from about 3 mm to about 5 mm. The length of the retention portion is more preferably about 6 mmn and the length of the delivery portion is more preferably 4 mm. However, these lengths depend on the particular material so the delivery portion may merely range in length from about 1 mm to about 3 mm.

The diameter of the pad is preferably about 7 mm to about 1 cm, and is most preferably about 8 mm. This diameter is sufficiently large to enable large amounts of treatment composition to be delivered and provides sufficient surface area to contact a cold sore or other disordered tissue as need. More particularly, a pad diameter that roughly corresponds with the diameter of a cold sore in its various stages of development is ideally configured to vigorously agitate the cold sore treatment site.

In addition to a pad that is a folded sheet formed from a web of fibers, the pad may also be formed from a cluster of aligned bristles. Factors related to selecting appropriate bristles include the rigidity and flexibility of the bristles based on the properties of the material used to form the bristles, the length of the bristles especially the delivery portion, and the diameter of the bristles. Another factor is the diameter of the cluster. All of these factors are balanced so that the cluster of aligned bristles enables the treatment composition to be delivered while preventing passage of glass shards and so that the cluster of aligned bristles may be used in a scrubbing action. So while the cluster of aligned bristles may be held in place much like a brush and may be configured to brush the composition onto the disordered tissue, the bristles are preferably sufficiently rigid for scrubbing the disordered tissue as the treatment composition is delivered. Such rigidity is preferably achieved through selecting a material, such as nylon, that is relatively rigid even when the bristle formed from the material has a relatively small diameter. Use of bristles having relatively small diameters is preferred to enable the cluster to scrub while minimizing any potential for injuring the disordered tissue. For example if the bristles are formed from nylon and are about 1 cm long so that the retention portion and the delivery portion are each about 5 mm long then the diameter may range from about 0.1 mm to about 0.2 mm, and is more preferably 0.15 mm.

Note that the treatment composition flows more easily through a pad that is a cluster of bristles than it does through a compressed sheet formed from a web of fibers. Also, less treatment composition is retained by a cluster of bristles. Accordingly, the frangible ampule need not contain as much treatment composition when the pad is a cluster of bristles.

An advantage of applicator 10 is that frangible reservoir 14 holds a relatively large volume of the treatment composition so that the treatment composition is delivered in an amount that is relatively large compared with the surface area to be treated. Further, the delivery is rapidly achieved due to the design of applicator 10 without requiring rewetting of pad 12 as the treatment composition is continually delivered to pad 12 until it is all used. For example, frangible reservoir 14 may deliver about 0.2 ml to about 1 ml to an area that is no greater than about 1 $cm^2$. Accordingly, the volume to surface area ratio is preferably in a range from about 0.2 $ml/cm^2$ to about 1 $ml/cm^2$. Such quantities are ideally sufficient to saturate the stratum spinosum 34 in the region of the cold sore or other disordered tissue so that it is available as a protective bath around the nerve. In any event, the treatment composition is preferably delivered in sufficiently large quantities that the disordered tissue at least appears moist and preferably such that the treatment composition pools initially on the surface of the disordered tissue. As indicated above, the penetrating capabilities of the treatment composition enables it to be no longer visibly detectable on the disordered tissue within several minutes after delivery of the treatment composition onto the disordered tissue.

A suggested application procedure using applicator 10 is to apply the 0.6 ml of the treatment composition for 30 seconds or longer, preferably while vigorously agitating the skin. Typical pain relief is within minutes. It may also be advantageous, especially during the prodromal stage, to deliver half of the treatment composition while rubbing the cold sore or other disordered tissue for about 30 seconds, wait about 1 minute and then deliver the remainder while rubbing for about 30 seconds again. Typically a single application is all that is required per outbreak, if the pain is not gone, or healing started in 24 hours then the treatment composition should be reapplied.

Figure 3:
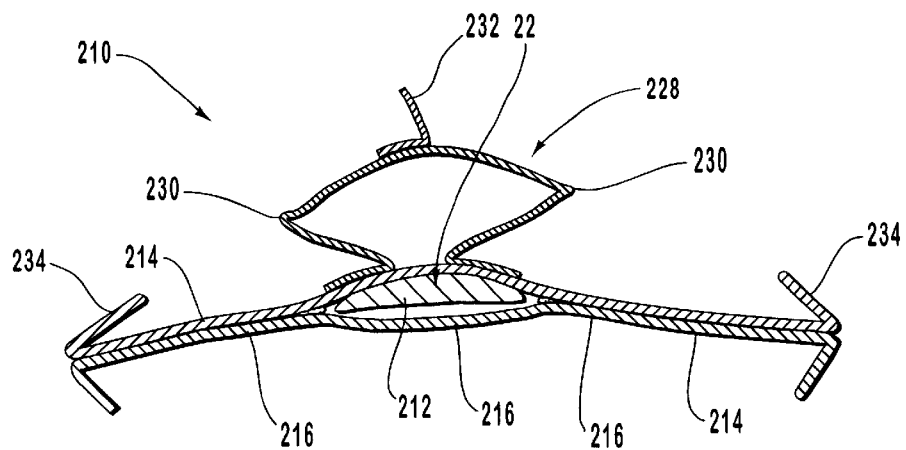
FIG. 3 is an elevational cross section view of an applicator that has a finger loop for vigorous topical irritation of the treatment site.

Another preferred applicator is illustrated in FIG. 3. FIG. 3 is a cross-sectional elevational view of an applicator 210 that may be part of the inventive system and method. Applicator 210 includes an absorbent agitation pad 212 that may be typical of a sterile adhesive bandage. Applicator 210 also includes adhesive wings 214 that may have adhesive typical of a sterile adhesive bandage. A separate strip acts as a container 216 in order to cause treatment composition 22 to remain in agitation pad 212 until container 216 is stripped away from adhesive wings 214 of applicator 210. In addition thereto, a finger loop 228 that may include finger loop folds 230 and a finger loop tab 232 is attached to applicator 210 immediately above agitation pad 212. Finger loop 228 is configured to lie flat against adhesive wings 214 and can be opened by lifting on finger loop tab 232 and hinge open at finger loop folds 230. Applicator 210 may be applied to a treatment site as typical of a sterile adhesive bandage and left in place indefinitely. Additionally, after a selected time period of having applicator 210, particularly agitation pad 212, upon a treatment site, the medical professional or the patient may grab the adhesive wing tabs 234, and gently pull adhesive wings 214 away from the skin. Meanwhile, the medical professional or the patient may insert a finger into finger loop 228, draw adhesive wings 214 also toward finger loop 228 and commence to vigorously agitate the disordered tissue.

Where it is preferable to immediately agitate the cold sore, applicator 210 may be applied at the point of agitation pad 212 onto the disordered tissue and then vigorously agitated against the disordered tissue. Thereafter, applicator 210 may be discarded or adhesive wings 214 may be applied to the patient's skin to allow applicator 210 to remain over the disordered tissue. This alternative may be preferable where bleeding is incidental to the inventive method. As such, applicator 210 doubles as an adhesive sterile bandage.

In summary, applicator 210 may be used for vigorous irritation of the disordered tissue or merely as a delivery applicator. It may be used initially for application of the anti-infective active agent without vigorous irritation of the disordered tissue which is then followed by vigorous irritation of the disordered tissue. Vigorous irritation by applicator 210 of the disordered tissue may be alternatively followed by leaving applicator 210 in place like a sterile adhesive bandage.

Figure 4:
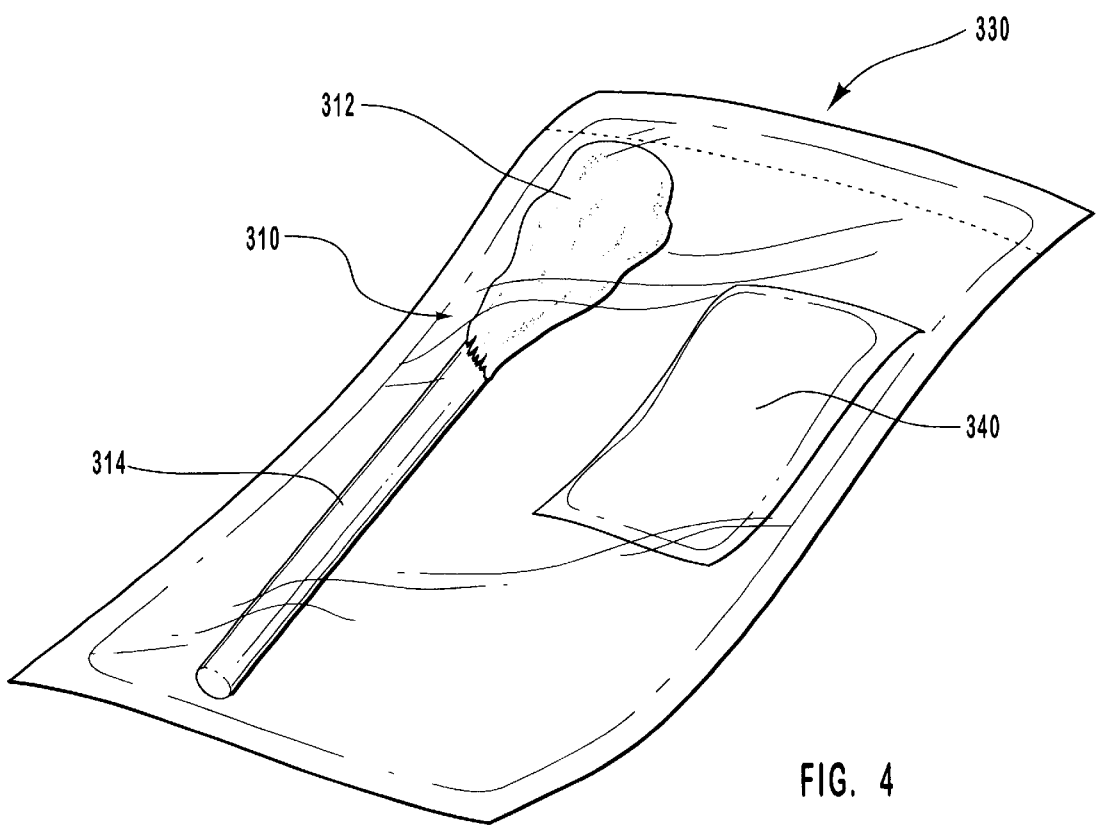
FIG. 4 is an elevational side view of an alternative applicator used in the present invention.

FIG. 4 depicts another applicator at 310 in an elevational side view which may be used in an alternative embodiment of the present invention. The applicator or cotton swab depicted at 310 has a swab agitation pad 312 upon a stem 314. Stem 314 may be formed from any suitable material, however, it is preferably relatively rigid to enable agitation pad 312 to be pushed and/or moved in the desired manner. Pad 312 is preferably used such that the side thereof is pushed against the disordered tissue and not the bulbous tip. The side is used so that sufficient pressure can be applied while using the tip presents certain difficulties. More particularly, when significant pressure is applied, the bulbous tip is likely to dig into the disordered tissue while the surrounding area receives less pressure. Additionally, use of the bulbous tip results in a smaller surface area being contacted which may require agitating different portions sequentially.

It is preferable that the use of swab agitation pad 312 be used under substantially sterile conditions so as to not introduce pathogenic elements into the treatment site of the disordered tissue. The sterile agitation pad of the swab may be dipped into the inventive composition and then used to abrade the skin. More preferably, the swab is held in a bag as shown at 330 which also holds a burst pouch as shown at 340. Burst pouch 340 holds the treatment composition and is sized and/or positioned within the bag such that upon bursting it saturates the cotton swab. An example of a bag holding a swab and a burst pouch designed to be frangible is disclosed in U.S. Pat. No. 5,709,866 to Booras, which was previously referenced.

An applicator and a burst pouch may also be held in separate compartments of a bag such as bag 330 with a perforated divider. Similarly, an applicator and a frangible reservoir such as frangible reservoir 14 may be held in separate compartments. The advantage of this arrangement is that the burst pouch or frangible reservoir can be ruptured to enable the treatment composition to flow into contact with applicator. When a frangible glass reservoir is used, the perforation prevents glass from contacting the applicator.

Fibers such as cotton are not preferred for holding the treatment composition while agitating the disordered tissue as extended exposure to cotton appears to reduce the efficacy of the methodology. Accordingly, when swab agitation pad 312 is formed from cotton, it is preferred that the pad not be stored in contact with the treatment composition. The use of a container such as burst pouch 340 when swab agitation pad 312 is formed from cotton achieves this objective. Applicators such as a swab may be stored in the same container as the treatment composition when swab agitation pad 312 is formed from synthetic materials, naturally occurring fibers which do not reduce the efficacy of the methodology, or fibers such as cotton which have been appropriately treated. Examples of suitable fibers include those discussed above in reference to applicator 10. Examples of a single bag or container for holding a swab are disclosed in U.S. Pat. No. 5,704,906 to Fox and U.S. Pat. No. 4,952,204 to Korteweg which were both previously referenced. Note that bag 330 and burst pouch 340 may be formed from any suitable materials and in any suitable manner.

Due to the relatively smooth texture of the cotton portion of most conventional swabs, when such swabs are used it is typically necessary to apply much more pressure than when an applicator such as applicator 10 or 210 is utilized. Additionally, an applicator such as applicator 10 is firther preferred as applicator 10 enables the treatment composition to be continuously delivered without requiring rewetting as a swab may. Further, swab agitation pad 312 holds only small quantities of the treatment composition so it is necessary to rewet it in order to deliver large volumes of the treatment composition. This prevents swab agitation pad 312 from rapidly delivering large quantities of the treatment composition.

The swab agitation pad may be replaced with a sponge to agitate disordered tissue. An example of a foam pad or sponge mounted on a stick such as stem 314 is disclosed in U.S. Pat. No. 4,887,994 to Bedford which was previously incorporated. Reference is made in U.S. Pat. No. 4,887,994 at column 2, lines 44–46 to coarse foam pads, such coarse foam pads are preferred for use as an agitation pad in accordance with the present invention. Coarse foam pads enable the disordered tissue to be more easily agitated through combined rubbing and application of an appropriate amount of pressure than softer foam pads. The coarse foam pad may also be utilized with a stick or stem.

Like the swab shown at 310, the other embodiments discussed above may be stored and used in a similar manner. More particularly, the coarse foam pad on a stick, the coarse foam pad alone, or a towelette may be held in a bag or other sterile container such as is shown at 330 along with a burst pouch as shown at 340. Additionally, these applicators may be held in a bag such as bag 330 without a burst pouch 340 in a dry sterile condition for dipping into a separate reservoir of the treatment composition or the treatment composition may be held in the bag along with the applicator.

Figure 5:
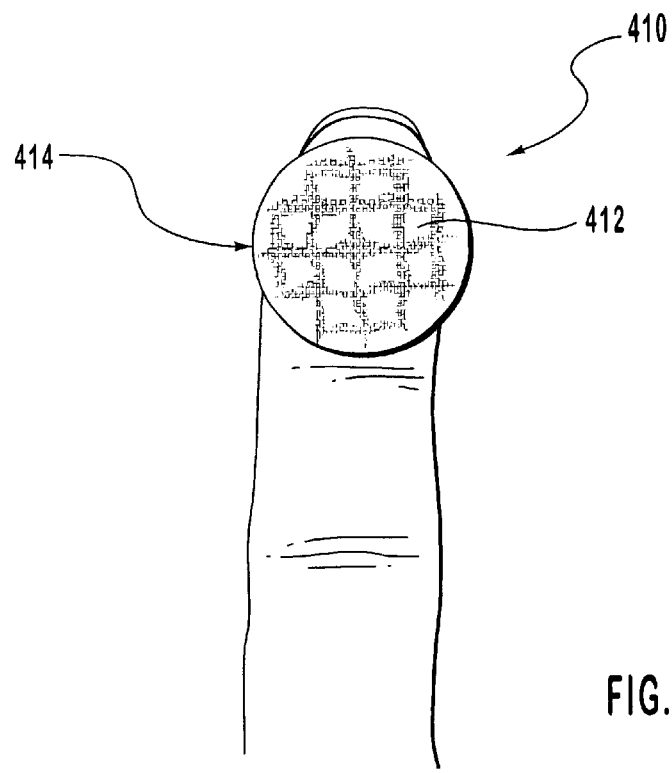
FIG. 5 is an elevational side view of an alternative applicator that is fixed to a digit for vigorous topical irritation of the treatment site.

FIG. 5 is an elevational perspective view of an alternative applicator that includes a fingertip applicator 410. Fingertip applicator 410 includes an absorbent, agitation pad 412 held on an adhesive surface 414 that the individual being treated or the medical professional applies to the fingertip. Agitation pad 412 may include an absorbent material for retaining the treatment composition and it may alternatively contain fixed abrasive elements to assist in the vigorous irritating of the disordered tissue at the treatment site.

Figure 6:
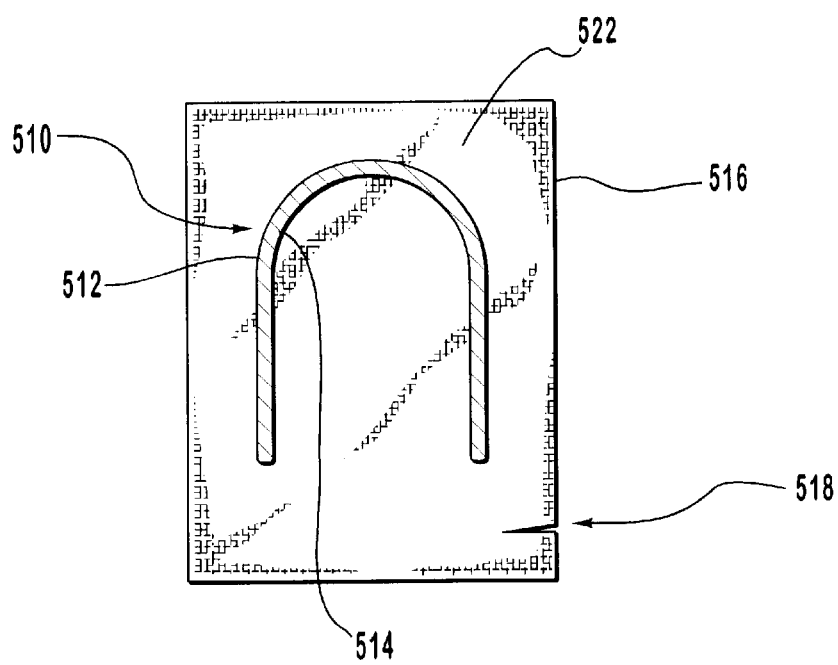
FIG. 6 is a cross-sectional plan view of an alternative applicator that is placed over a digit and that is contained in a pre-wetted state before use.

FIG. 6 is an elevational cross-section view of an alternative applicator that includes a finger- or digit-container applicator 510. Digit-container applicator 510 includes an absorbent, agitation pad 512 with a first side 512 that acts as the agitation pad 516, and a second side 514 that acts at the support 514. The user may rupture the container 516 such as by tearing a slit 518 and inserting a finger into applicator 510 against second side 514. Container 516 is a bag like that shown at 330 and may be referred to as what is commonly called a pillow pouch or package. Container 516 may also contain a burst pouch such as burst pouch 340. Applicator 510 is, however, preferably pre-moistened by the presence of treatment composition 522 within container 516. Applicator may also be held in a container 516 in a dry sterile condition for dipping into a separate reservoir of the treatment composition.

First side 512 is made of an absorbent and abrasive material that is substantially uniform in relation to the size of a disordered tissue site. First side 512 preferably has the approximate roughness of a conventional gauze bandage or terry cloth. However, first side 512 and/or second side 512 are not necessarily formed from cotton. In fact, as discussed above, cotton is preferably not used unless it has been appropriately treated not to absorb the treatment composition, particularly the benzalkonium chloride.

Preferably, first side 512 is seamless and devoid of fabric folds etc. Additionally, where second side 514 is used to interface with a finger, it is a support for first side 512 as the agitation pad and delivery portion of applicator 510. As a structural explanation of applicator 510, if applicator were to be turned inside-out, first side 512 would be under compressive stress and second side would be under tensile stress.

Like the other applicators, applicator 510 can have varying sizes depending on its intended use. For example, if applicator 510 is used to deliver the treatment composition to a cold sore then it is large enough to enable at least one fingertip into it. However, if applicator 510 is used to treat the sores caused by shingles on, for example, an individual's back or other large surface of the body then it may be useful for applicator 510 to be large enough so that several fingers or even the entire hand can fit inside it like a mit. Such a mit sized applicator enables the treatment composition to be rapidly delivered to large surface areas.

Figure 7:
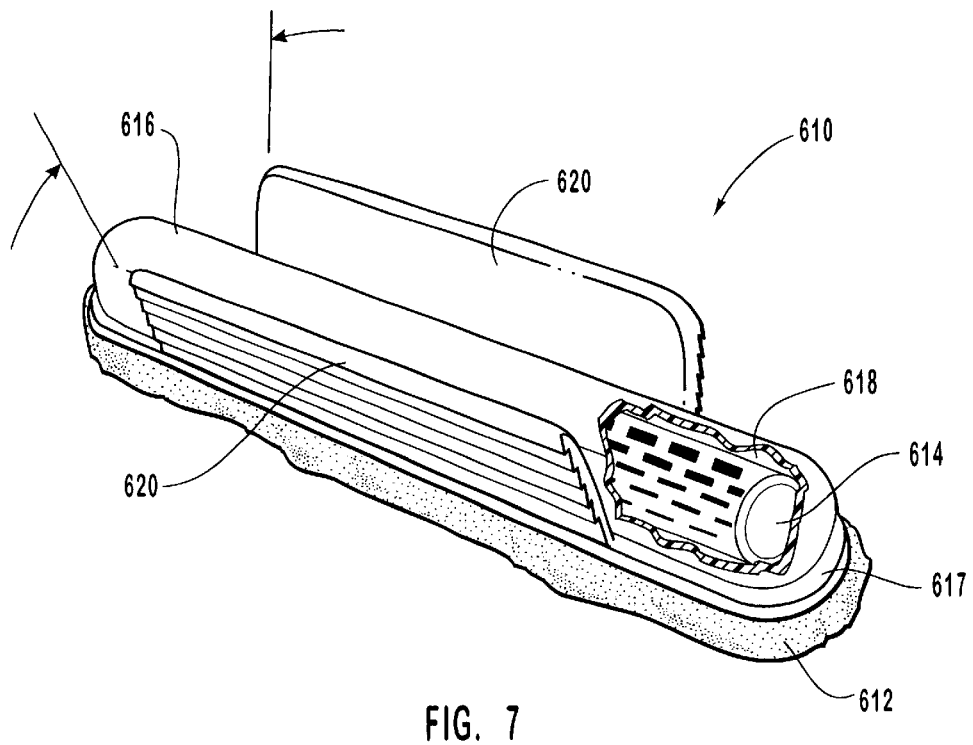
FIG. 7 is a perspective view with a partial break-away view of an alternative applicator that is used to apply the treatment composition to large surface areas of the body.

FIG. 7 depicts another embodiment of a system for delivering a treatment composition to disordered tissue. Like the mit sized version of applicator 510, applicator 610 is very useful for treating large surfaces of the body such as a patient's back. Applicator 610 comprises only four main components: the treatment composition that is contained in a large frangible ampule 614 or reservoir, the container 616 and pad 612 hold frangible ampule 614 in place.

Container 616 has thin-walls at recess 618, the closed end opposite from open delivery end 617, into which frangible ampule 614 is positioned. When applicator 610 is ready for use, handle wings 620 are squeezed until they compress the thin sidewalls of container 616 inward at recess 618 such that pressure is applied to frangible ampule 614 such that ampule 614 ruptures. The treatment composition is then released and flows into pad 612.

Frangible ampule 614 preferably contains a volume of the treatment composition ranging from about 0.5 ml to about 4 ml. The volume preferably ranges from about 1.5 ml to about 3 ml and more preferably about 2 ml to about 3 ml.

Pad 612 is adhered to the rim of open delivery end 617 of container 616 through any suitable means such as an adhesive, heat fusion, or a mechanically interlocked configuration. Pad 612 prevents shards from the rupture ampule from passing through and causing injury. Once pad 612 is adequately moistened then it can be used to rapidly apply the treatment composition to large surface areas as shown in FIG. 8. FIG. 8 depicts the use of applicator 610 to apply the treatment composition to a patient's chest afflicted with sores from shingles.

Applicator 610 can be used to merely deliver the treatment composition without any vigorous agitation. Applicator 610 can also be used to apply pressure and/or scrub the surface area to which the treatment composition is being or has been delivered. Note that abrasiveness of pad 612 can be varied significantly to achieve varying degrees of ability to vigorously agitate the disordered tissue. Another example of an applicator that has a container that also acts as a handle, a glass ampule positioned in the handle and a porous pad is disclosed in U.S. Pat. Nos. 4,183,684, 4,183,684 is hereby incorporated by reference. Not only are such applicators are able to deliver the treatment composition to large surface areas of the body, it is delivered rapidly in large quantities without requiring rewetting.

FIGS. 9–11 depict a towelette being used as an applicator to treat various disordered tissue. The towelettes depicted at 710 may be a relatively smooth towelette or a relatively abrasive towelette, the towelettes can also have varying thicknesses. Towelettes are generally not as useful as other applicators in treating disordered tissue as they require a large quantity of the treatment composition in order to be wetted and yet deliver only a small quantity of the treatment composition to the disordered tissue. However, the ability to hold a greater volume of the treatment composition can be increased by increasing the thickness of the towelette. Additionally, the towelette can be repeatedly dipped to rewet it. For example, FIG. 9 depicts a user with a finger wrapped in a towelette that is being used to deliver the treatment composition to a cold sore on the user's lip. The user can then rewet only the portion of towelette 710 being used to apply pressure to the cold sore.

Note that while it is less effective to use a towelette as compared with an applicator such as applicator 10 since the towelette cannot be used to rapidly deliver a large volume of the treatment composition it can still serve several functions. As discussed above, a towelette may be used to preclean the disordered tissue or to deliver an anesthetic. Precleaning disordered tissue with a towelette, especially an abrasive towelette, may be useful to awaken the immune response for a synergistic effect once the disordered tissue is vigorously agitated. The abrasive surface towelette also has the advantage of removing tissue that is in the process of sloughing off from the disordered tissue site. Such tissue may provides a hindrance to the inventive method because it restricts penetration of the anti-infective active agent to living disordered tissue.

The towelette may be used to deliver the treatment composition even if it is not as effective as applicators used to rapidly delivering a large quantity of the treatment composition. A smooth towelette is generally ineffective in rubbing the disordered tissue as it has inadequate roughness to agitate the disordered tissue by rubbing it, however, it can be used to push against the disordered tissue. For example, if towelette 710 is relatively smooth then the user shown in FIG. 9 may dab the cold sore with the treatment composition soaked towelette or the user may apply pressure to the cold sore. Use of a towelette that has a thickness and smoothness that is comparable to that of ordinary handwipes may be scrunched in order to better hold the towelette while dabbing the disordered tissue and to concentrate the moisture held in the towelette. Such a scrunched smooth towelette may result in folds, so it should not be rubbed against the disordered tissue as it may dig into the disordered tissue, particularly if it is an open sore. In any event, folds resulting from drawing the towelette together prevent the towelette from being used to uniformly agitate disordered tissue through rubbing. If a towelette is be rubbed against the disordered tissue, then it is preferable to use an abrasive towelette.

As indicated above, the abrasive towelettes are distinguished from conventional towelettes used for cleaning hands, etc. In addition to being too smooth, conventional towelettes are also typically too thin to hold adequate amounts of moisture while an abrasive towelette preferably has sufficient thickness to hold adequate amounts of the treatment composition. Of course, smooth towelettes with increased thickness can also be used. The abrasive towelettes can also have increased thickness to hold more treatment composition.

The towelette fiber may be formed from fibers such as those discussed above in reference to applicator 10 or any of the other applicators. The towelette may be selected from existing stock formed from treated natural fibers, synthetic fibers, and untreated natural fibers. One example of an abrasive towelette is a rough paper towel used in the paper towel industry or the like. One of ordinary skill in the art may select a towelette that has the preferred abrasive qualities while maintaining a preferred absorbability in order to convey the anti-infective active agent to the disordered tissue treatment site.

FIG. 10 depicts towelette 710 being used in the genital area. An advantage of using a towelette for delivering the treatment composition in the genital area is that the towelette is able to conform to the various surface features and it enables the user to deliver the composition with sensitivity to the more sensitive parts in the genital area of the body. As with the other applicators, the towelette is disposed of after a single use to prevent the spread of substances contained in the disordered tissue.

FIG. 11 depicts towelette 710 being used to deliver the treatment composition to a patient that has sores from shingles on his chest. Since the skin on body parts such as the chest, arms, the back, etc. are thicker than it is on the lips, use of a towelette is especially less effective than use of an applicator such as applicator 610. It may however be useful to preclean the disordered tissue in this manner. Essentially, towelettes are primarily ideal for areas of the body that have surfaces areas that are not primarily flat or that have irregular surfaces such as the genital area. The towelette is ideal for these areas as it can access all areas without causing pain.

The towelette may be held in a bag such as the bag shown at 330 which also holds a burst pouch as shown at 340. Burst pouch 340 holds the treatment composition and is sized and/or positioned within the bag such that upon bursting it saturates the towelette. The bag may hold the towelette and the burst pouch in a similar fashion to the designs disclosed in U.S. Pat. No. 5,709,866 to Booras, which was previously referenced. The towelette and a burst pouch may also be held in separate compartments of a bag such as bag 330 with a perforated divider. Depending on the material used to form the towelette, it may be advantageous to either separately store the towelette and the treatment composition, as discussed above, or to store them together in the same container, especially when the towelette is formed from synthetic materials. As discussed above, examples of a single bag or container for holding a towelette are disclosed in U.S. Pat. No. 5,704,906 to Fox and U.S. Pat. No. 4,952,204 to Korteweg which were both previously referenced. Towelette 710 may be dipped into a separate reservoir and then used to deliver the treatment composition.

The above embodiments comprise examples of an inventive method and system of treating disordered tissue. It is preferred not to dip a bare finger into a container of the treatment composition because oils or other materials contained on the finger may be of sufficient amount to cause the treatment composition to be rendered ineffective. Additionally, back contamination of composition in the container may occur. The agitation pads 12, 212, 312 412, 612 as well as first side 512 are examples of a delivery and agitation means for delivering the treatment composition and for agitating the disordered tissue of the patient. Note that other examples include an abrasive towelette and a coarse foam pad. As discussed above, a conventional smooth towelette is not an example of a delivery and agitation means capable of being used to rub the disordered tissue.

The container 16 of applicator 10, the finger loop 228 of applicator 210, the stem 314 of applicator 310 or similar applicators, the adhesive surface 414, the second side 514 of applicator 510 and the container 616 of applicator 610 are examples of a means for supporting the delivery means.

A coarse foam pad, pad 212, pad 412, first side 512, pad 612 and abrasive towelette 710 are all examples of delivery and agitation means capable of conforming to the surface features of the disordered tissue as the corresponding supporting means also conforms to the surface features. Stated otherwise, the applicator is flexible such that both the delivery and agitation means as well as the supporting means flex in conformance with the surface anatomy of the disordered tissue. First side 512 is particularly useful for adapting to the a surface anatomy of the disordered tissue. Pad 612 can also be thick enough to conform to various surfaces features of the body area being treated.

The frangible reservoir 14, container 216, container 516 and frangible ampule 614 are examples of a reservoir means for containing the composition. Additionally, a bottle or the like that contains treatment composition 22 for use with applicator 310 is another example of a reservoir means for containing the composition. Note that reservoir 14, container 216, container 516, and ampule 614 however, are configured to be in fluid communication with the delivery and agitation means. Frangible reservoir 14, burst pouch 340 and frangible ampule 614 are configured to be in fluid communication with the delivery and agitation means once ruptured. Frangible reservoir 14 and frangible ampule 614 are further configured to continually deliver the treatment composition to the delivery and agitation means while the delivery and agitation means is agitating the disordered tissue until all of the treatment composition has been delivered. Note that one of the primary distinctions between frangible reservoir 14 as compared with burst pouch 340 is that the frangible reservoir 14 is located within the container 16. Similarly, frangible ampule 614 is located within container 616.

Container 516 and bag 330 are examples of container means for holding the applicator. This configuration, as discussed above, enables the applicator to be held in a dry sterile condition for dipping into a separate reservoir of the treatment composition. As also indicated above, container 516 and bag 330 can also hold the treatment composition along with the applicator such that the applicator is premoistened. Accordingly, container 516 and bag 330 are also examples of container means for holding the applicator and the treatment composition. As further indicated above, container 516 and bag 330 can also hold the treatment composition in a pouch along with the applicator. On this basis, container 516 and bag 330 are also examples of container means for holding the applicator and a reservoir means.

The inventive method of treating disordered tissue and the like includes impregnating an applicator with the inventive anti-infective composition and contacting the treatment site with the applicator. Vigorous agitation of the disordered tissue is particularly useful as the induced physical trauma causes the awakening of the bodys immune response local to the irritation. As such, the immune response and the penetration of the inventive composition into the disordered tissue has the concerted effect of a rapid decline of the infection.

Chemotaxis, the migration of phagocytes such as granular leucocytes and human leucocyte associated (HLA) antigens to an area of a tissue disorder, is enhanced and assisted in the present invention by the vigorous agitation of the disordered tissue with the anti-infective active agent or agents. The combination of the anti-infective active agent, preferably benzalkonium chloride, with the chemotaxis phenomenon caused by the vigorous agitation of the disordered tissue, has the surprising effect of a rapid decline of the infectant such as a virus or a microbe in the disordered tissue. Note that one type of granular leucocyte, the neutrophil, has the ability to activate defenses which are amino acids that exhibit abroad range of antibiotic activity against bacteria, fungi, and viruses. Consequently the synergistic effect of vigorous agitation is rapid delivery and the awakening of the immune response. The neutrophil, if activated is therefore useful to treat disordered tissue according to the present invention where bacteria, fungi, or virus infections occur. Further, agitation causes fluids to concentrate in the area of the disordered tissue which further enables the active agent to move as needed in order to penetrate effectively.

Other immune responses may occur with the vigorous agitation of the disordered tissue site by the inventive method, and the inventors do not wish to be bound to any single theory that may explain the surprising efficacy of the inventive method and system

EXAMPLES OF THE PREFERRED EMBODIMENTS

The following examples are provided as illustrative of the inventive method and system. These examples are not intended to be limiting of the invention. The examples all produce clinically discemable improvement of disordered tissue. By "clinically discemable improvement of disordered tissue," it is understood that various testing methods may be used to quantify improvement of disordered tissue. One example of clinically discemable improvement of disordered tissue include arresting the normal progression of a tissue disorder such as a cold sore. Another example of clinically discemable improvement of disordered tissue is healing of a tissue disorder at a faster rate than was observed before in a recurrent disorder such as a cold sore. Another example of clinically discemable improvement of disordered tissue is an arrest of pain usually associated with the progression of a tissue disorder such as a cold sore. Another example of clinically discemable improvement of disordered tissue is the permanent deactivation of a recurrent tissue disorder site after the inventive method is applied to a disordered tissue site.

The clinical examples provide hereinbelow were performed with a treatment composition which included benzalkonium chloride. The carrier was 30% by volume water and 70% isopropyl alcohol by volume of the carrier. The treatment composition was prepared with about one part benzalkonium chloride to about 750 parts carrier. More particularly, 5 drops of benzalkonium chloride having a concentration of about 17% in isopropyl alcohol were added for each ounce of the carrier. The result was a treatment composition containing about 0.0133% benzalkonium chloride by volume of the treatment composition. Although additives and other constituents may be combined with the mixture as set forth above these particular test treatment compositions did not include any additives.

As discussed above, the methodology in the examples includes vigorously applying the composition to the disordered tissue and removing the superficial lipids by the carrier. The carrier also is useful for the penetration of the disordered cells at the tissue disorder site. Either following or simultaneously with the penetration of disordered cells with the composition at the tissue disorder site, vigorous agitation of the tissue with the composition is carried out under conditions to increase the flow of intercellular fluid to the tissue at the tissue disorder site. This enables the active agent greater ease of transportation at the site to better penetrate.

CLINICAL EXAMPLES

Clinical Example 1

A male was diagnosed with several vesicles beginning to coalesce on the lip. Treatment was initiated immediately. After about 1 day, it was observed that the vesicles had not coalesced further and that progression of the cold sore through its normal stages was arrested. After about two days, scab tissue was observed to be sloughing off. After about seven days, no sign was left of the disordered tissue. The patient observed that for previous eruptions the complete healing of this cold sore at this site took from about two to three weeks.

Clinical Example 2

A male was diagnosed with a cold sore erupting below the corner of the mouth. The usual tingling and tightening sensation that occurs with a cold sore onset was observed by the patient. The inventive composition and method was applied to the patient according to the inventive method. Immediately upon application, the usual tingling and tightening sensation was not noticed. After about two days, no visible sign of a cold sore was observable.

Clinical Example 3

A male with a history of cold sores ranging in a size from about 1.5 cm to about 2.5 cm in diameter was treated immediately upon sensing the tingling and tightening of an oncoming cold sore. A numbing sensation was immediately noticed and the pain was gone. After about 3 days, the cold sore had begun to heal.

Clinical Example 4

A female was diagnosed with pustules and vistules upon the lower lip. The inventive composition was applied to the patient according to the inventive method, and pain was gone as soon as the application of the inventive composition was done. Instead of the normal weeping and scabbing the patient was used to, the cold sore healed without weeping or scabbing, and pain was minimal in comparison to previous experiences.

Clinical Example 5

A female had a disordered tissue eruption upon a digit with about 7 vistules in the pre-eruption stage. The blistering typical of this type of tissue disorder began to fade immediately after application of the inventive composition. A small amount of scaling was observed after about 2 weeks. The patient observed that the normal course of an eruption and healing at this cold sore site was shortened by the inventive composition and method.

Clinical Example 6

A female was diagnosed with a cold sore taking up about one-half of the area of the lower lip. The cold sore had multiple lesions. The inventive composition was vigorously applied to the cold sore. Pain was immediately relieved and weeping was immediately arrested from the cold sore.

Clinical Example 7

A female observed tingling and tightening upon the inside of her lip in the evening and observed one small pustule and three to four vistules at the time of treatment the next morning. The inventive composition was applied by vigorous rubbing with a cotton swab. A second treatment was carried out that evening, and a third treatment was carried out the following morning. The pain was observed to be relieved fairly quickly upon the first treatment. The patient observed that the inventive composition and method worked at least as well as her usual Zovirax® prescription, manufactured by Glaxo Wellcome Inc. of Research Triangle Park, N.C. The following advantages of the inventive composition and method were observed in comparison. One advantage was that fewer applications were required. Additionally, no unpleasant tasting ointment remains upon the lip during the treatment time.

Clinical Example 8

A female with a cold sore history including at least one eruption per month was diagnosed with some yellow scabbing present upon a cold sore site. After vigorous irritation of the disordered tissue with the inventive composition, the patient observed that pain was completely gone after about seven hours.

Clinical Example 9

A male was diagnosed with a cold sore upon the lower lip. The inventive composition was applied by rubbing. The cold sore was observed to be healed after two days.

Clinical Example 10

A male was diagnosed with a number of cold sores at the corner of the mouth and above the lip. Prior to vesicular eruption, the usual pain that precedes the eruption of a cold sore was observed about 24 hours previously. The inventive composition was applied by rubbing. Growth of the disordered tissue was immediately arrested and the tissue appeared to have cleared in three days following the treatment.

Clinical Example 11

A female diagnosed with a cold sore upon the chin about halfway between the base of the chin and the lower lip. The inventive composition was applied with rubbing. The cold sore was observed to have healed within about two days.

Clinical Example 12

A six year old female was diagnosed with an open cold sore upon the lower lip. The inventive composition was applied by vigorous rubbing. The cold sore was barely observable in about three days.

Clinical Example 13

A male was diagnosed with a cold sore upon the lower lip. The inventive composition was applied by vigorous rubbing. The progression of the cold sore was arrested and pain was stopped within a few minutes.

Clinical Example 14

A female was diagnosed with a cold sore at the corner of the mouth that would crack when the mouth was opened. The inventive composition was applied by vigorous rubbing. Within about two days, the cold sore was observed to be completely healed. The patient observed that cold sores in the corner of the mouth of this type usually took at least 7 to 10 days to heal.

Clinical Example 15

A three-year old male was diagnosed with a cold sore upon the lip. The inventive composition was applied by vigorous rubbing. It was observed that progression of the cold sore was immediately arrested and that the cold sore did not form at that site again. The patient had about six sites that erupted upon the lips frequently, and no treated site re-erupted after treatment.

Clinical Example 16

A four-year old male with a history of about 25 oral cold sores was treated by vigorous agitation of the disordered tissue upon a re-eruption of each untreated cold sore. Pain was observed to cease immediately upon treatment. Additionally, the cold sore did not erupt again at any of the specific treatment sites even after a year.

Clinical Example 17

A male was diagnosed with a cold sore below the corner of the lower lip. The inventive composition was applied by vigorous rubbing. Immediately upon application, the tingling sensation that accompanied the cold sore was gone. The next morning the cold sore had closed and was scabbed and healing. Within two days of the application, the cold sore was completely healed. The patient observed that normal healing time, before the inventive treatment, took about two weeks.

Clinical Example 19

A male was diagnosed with a cold sore in the vistial stage upon the lower lip. The inventive composition was applied by vigorous rubbing. The cold sore was observed not to progress beyond the vistial stage. Healing occurred without pain and throbbing. The cold sore was totally healed within seven days.

Clinical Example 20

A female was diagnosed with two cold sores upon the lower lip. The inventive composition was applied by vigorous rubbing between about 30 and about 60 seconds. No pain was felt after the vigorous rubbing. Two days later, one of the cold sores was gone and the other one had a slight scab that was also gone after three more days.

Clinical Example 21

A female was diagnosed with a cold sore that was about 2 cm across and generally round in shape, below one corner of the lower lip. The inventive composition was applied by vigorous rubbing. The patient described the cold sore to be burning and weeping. Within about one minute of treatment, the burning had stopped. Within hours, the weeping stopped and a normal or non-cold sore scab appeared. Within days, the cold sore was gone and healed. No re-occurrence of the cold sore was observed.

Clinical Example 22

A male was diagnosed with an extremely swollen, red and weeping cold sore above one eye. The inventive composition was applied by vigorous rubbing to the cold sore. The swelling and redness were reduced within minutes of the treatment. By the next morning, the cold sore appeared to be a normal or non-cold sore scab. Complete healing was observed after about four days.

Comparative Clinical Example 1

A female was diagnosed with a cold sore above the upper corner of the upper lip. The inventive composition was applied but only slight rubbing occurred. Soap was used on the cold sore treatment site that evening. Although the cold sore formed a scab after about two days, a new cold sore erupted at that time above the existing scab and spread itself into the scab.

Clinical Example 21

A female was diagnosed with a canker or ulcer. The inventive composition was applied by vigorous rubbing until blood was seen on the cotton swab. The patient observed that the canker was gone after only about two or three days. When the patient was re-examined one week after the treatment, there was no sign of the canker.

Clinical Example 22

A male was diagnosed with shingles in two eruptions; one upon the face over the cheekbone and the other upon the back of the neck. The inventive composition was applied by vigorous rubbing to the eruption upon the face. Immediate reduction in discomfort was observed. The redness also immediately began to fade. The patient used shaving soap the same day following treatment and observed that the eruption on the face was returning. A second treatment was repeated in the same manner and progress was again arrested. The treatment site was not contacted the second time with any soap. The eruption on the face healed completely while the eruption on the back of the neck remained even after about four weeks. Treatment was carried out on the eruption on the back of the neck and the eruption was healed in a few days.

Clinical Example 23

A female was diagnosed with a rash of shingles across the midsection above and at the naval. The inventive composition was applied by extensive and vigorous rubbing for about 20 minutes. The progression of the rash was immediately arrested and no new outbreaks were observed. The rash had been growing from small spots into large sores.

Clinical Example 24

A number of patients with primary eruption cases were treated by the inventive method. It was observed that in each patient, there was no reoccurrence of cold sores, as is typical with untreated primary occurrences.

Clinical Example 25

An individual was diagnosed with what appeared to be a spider bite upon the lower calf area of the leg from a Brown Recluse. A "bullseye" discoloration was observed at the bite location with a brown-red middle region and a red circumferential region. The entire area affected by the venom appeared to be about eight to about nine centimeters in diameter. The inventive composition was applied by vigorous rubbing. After an overnight wait following treatment, the discoloration was not observable. A scab that formed at the center of the bite, fell off after about three days.

Other ways to evaluate the progression of the cold sore healing process include measuring the size of the cold sore and also the degree of inflammation thereof One such method of evaluation is colorimetry of inflamed tissue that creates a color scale that has apparently healthy tissue of the patient as the baseline, and ranks the inflamed color with some external standard or that nominalizes the inflamed tissue such as being at a nominal red scale of 10. A "nominal red scale" is defined as assigning the tissue color a nominal 10; a nominal zero being undisordered tissue of the same type for the specific patient. Clinically discernable improvement of inflamed tissue is defined as reducing in the nominal red scale within about 24 hours by as much as about two or more on the nominal red scale of 10. With a disordered tissue having substantially no clinically discemable improvement of disordered tissue, a red scale decrease of below about one or less within 24 hours is observed.

Another method is the assay of eosinophils and other immnune response substances in the inflamed area before and after the inventive method of treatment. Where the presence of eosinophils and the like increases by more than about 10% within about one hour of the inventive method of treatment, as opposed to less than about 10% increase in eosinophils and the like with a control cold sore, a clinically discemable improvement has occurred.

The following are hypothetical examples. These hypothetical examples include treatment compositions utilizing organochlorides other than benzalkonium chloride. More particularly, these organochlorides include: benzethonium chloride, methyl benzethonium chloride, cetyl pyridinium chloride, chloroxylenol, hexachlorophene, triclosan, chlorhexidine. Their chemical structures are also provided to show that a variety of organochlorides which differ structurally may be utilized. These organochlorides are also used at various concentrations. Additionally, different carriers are utilized.

Example 1

In a first example, disordered tissue that has a redness of 10 of a nominal red scale is subjected to the inventive method by impregnating an applicator with about 0.02% benzalkonium chloride in isopropyl alcohol composition. The impregnated applicator is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined and is found to have a decreased nominal red scale to about 6 after about 24 hours and an increased eosinophil assay of about 40% before about one hour.

Comparative Example 1

In a first comparative example, an applicator with about 0.02% benzalkonium chloride in isopropyl alcohol is gently applied to a disordered tissue by dabbing such that substantially no pressure is applied sufficient to depress the tissue against hard tissue that lies underneath. The impregnated applicator is applied to a labial disordered tissue for a time period of about 30 seconds. During the application time period, about 0.1 ml of the inventive composition is absorbed into the patient's disordered tissue. The patient's disordered tissue is estimated to have an area of about 0.5 cm². The patient's disordered tissue is then examined and is found to have a decreased nominal red scale from 10 to about 9 after about 24 hours and an increased eosinophil assay of about 5% before about one hour.

Comparative Example 2

In another example comparative to the first example, a disordered tissue is treated substantially the same as in the first example with the exception that only isopropyl alcohol is impregnated in the applicator. The patient's disordered tissue is examined after the treatment and is found to have an unchanged nominal red scale score of 10 and a negligibly increased eosinophil assay. However, note that some reduction of redness occurs when just alcohol is used, especially when the disordered tissue is an open sore, as the alcohol tends to wash away toxic material. The redness returns as does the pain as toxins continue to build up since the source of the infection has not been eliminated. Note also that in the United States, alcohol cannot be listed as an active agent in the treatment of cold sores caused by herpes.

Example 2

In a second example, all conditions are the same as in the first example with the following variations. An embodiment of the inventive composition is applied to a typical sterile bandage and left over the patient's disordered tissue for about one hour. The sterile bandage may double as part of the applicator. The composition contains, in addition to about 0.02% benzalkonium chloride in isopropyl alcohol, about 5% of a composition of lidocaine and prilocaine in about a 1:1 mixture. After the one hour time period, the patient's skin is substantially numbed, and the applicator is vigorously rubbed into the disordered tissue for about 30 seconds. The patient experiences significantly less pain than that experienced in the first example. The patient's disordered tissue is then examined and is found to have a decreased nominal red scale to about 3 from a beginning of eight after about 24 hours and an increased eosinophil assay of about 50% before about one hour.

Comparative Example 3

In a second comparative example, all conditions are the same as in the second example except that no agitation of the disordered tissue occurs. The patient again experiences a numbing sensation after contact of the inventive composition with the cold sore, but is found to have a decreased nominal red scale to about nine and an increased eosinophil assay of about 10% before one hour.

Comparative Example 4

In another example comparative to the second example, the applicator is impregnated with the lidocaine: prilocaine mixture in isopropyl alcohol but no benzalkonium chloride or any other active agent is included. The patient's disordered tissue is then examined and is found to have a nominal red scale of about nine and a negligibly increased eosinophil assay before one hour.

Example 3

In a third example, a patient with pink eye is administered the inventive composition containing about 0.01% benzalkonium chloride in a carrier that is substantially nonirritating to the sclera and supporting eye tissue. The patient, with washed and disinfected hands, then rubs the closed eyelid with the hand or fingers for about 30 seconds. The patient's eye is then examined and is found to have a decreased nominal red scale to about 1 after about 24 hours.

Comparative Example 5

In a third comparative example, a patient is treated exactly as in the third example except that no rubbing through the closed eyelid is carried out. The patient's eye is then examined and is found to have a decreased nominal red scale only to about 7 after about 24 hours.

Comparative Example 6

In another comparative example to the third example, the patient with pink eye is administered with a carrier but with no active agent therein. The patient's eye is then examined and is found to have a decreased nominal red scale to about 8 after about 24 hours.

Example 4

In this example, a treatment composition is formed with benzethonium chloride as the active agent. Hereinbelow is the chemical structure of benzethonium chloride:

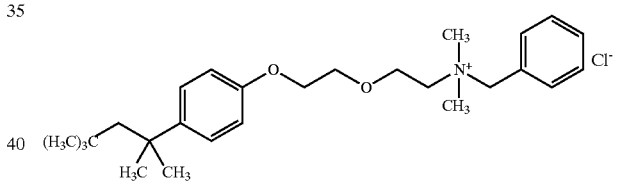

The treatment composition is applied to disordered tissue like that in Example 1 which has a redness of 10 or a nominal red scale. The disordered tissue was on the patient's back. Note that when the treatment composition is applied to thicker sections of skin such as occur on the back it is more difficult to penetrate than on thinner sections such as the lip or cheek. Accordingly when treating such thick skin portions, it is necessary to increase the active agent concentration, rub and/or press harder, or agitate more frequently. The treatment composition includes about 0.01% benzethonium chloride in isopropyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm². The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 5

In this example, a treatment composition is formed with methyl benzethonium chloride as the active agent. Hereinbelow is the chemical structure of methyl benzethonium chloride:

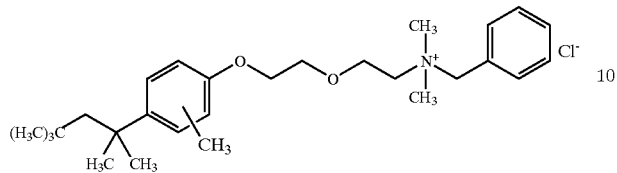

The treatment composition is applied to disordered tissue like that in Example 1 which has a redness of 10 or a nominal red scale. The treatment composition includes about 0.02% methyl benzethonium chloride in a carrier comprising about 70% isopropyl alcohol by volume of the carrier and about 30% water. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 6

In this example, a treatment composition is formed with cetyl pyridinium chloride as the active agent. Hereinbelow is the chemical structure of cetyl pyridinium chloride.

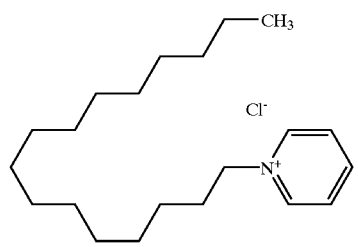

The treatment composition is applied to disordered tissue like that in Example 1 on a patient's arm which has a redness of 10 or a nominal red scale. The treatment composition includes about 2.0% cetyl pyridinium chloride in a carrier comprising about 60% isopropyl alcohol by volume of the carrier, about 30% water and 10% acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 7

In this example, a treatment composition is formed with chloroxylenol as the active agent. Hereinbelow is the chemical structure of chloroxylenol.

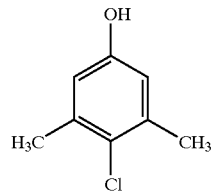

The treatment composition is applied to disordered tissue like that in Example 1 which has a redness of 10 or a nominal red scale. The treatment composition includes about 0.5% chloroxylenol in acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 8

In this example, a treatment composition is formed with hexachlorophene as the active agent. Hereinbelow is the chemical structure of hexachlorophene.

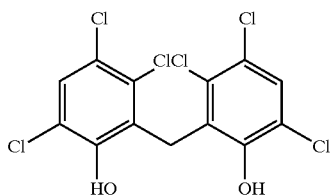

The treatment composition is applied to disordered tissue like that in Example 1 which has a redness of 10 or a nominal red scale. The treatment composition includes about 0.04% hexachlorophene in a carrier comprising about 80% isopropyl alcohol by volume of the carrier, about 15% water and 5% cetyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 9

In this example, a treatment composition is formed with triclosan as the active agent. Hereinbelow is the chemical structure of triclosan.

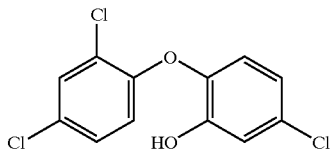

The treatment composition is applied to disordered tissue like that in Example 1 which has a redness of 10 or a nominal red scale. The treatment composition includes about 0.01% triclosan in a carrier comprising about 60% methyl alcohol by volume of the carrier, about 30% water and 10% acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

Example 10

In this example, a treatment composition is formed with chlorhexidine as the active agent. Hereinbelow is the chemical structure of chlorhexidine.

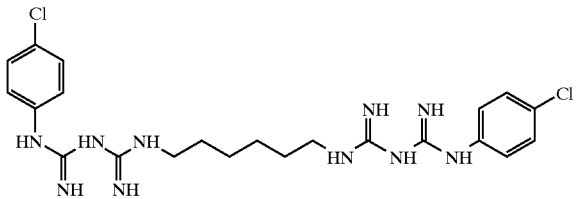

The treatment composition is applied to disordered tissue like that in Example 1 which has a redness of 10 or a nominal red scale. The treatment composition includes about 0.03% chlorhexidine in methyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A treatment composition for application to and penetration into disordered tissue, the treatment composition comprising:
   at least one anti-infective agent in a carrier,
       the anti-infective agent comprising an organohalide, and
       wherein the treatment composition is a liquid comprising a tissue penetrating component for penetrating skin in a rapid manner without rapidly diffusing beyond the skin.

2. A composition as recited in claim 1, wherein the at least one anti-infective agent consists essentially of an organochloride.

3. A composition as recited in claim 1, wherein the at least one anti-infective agent comprises at least one benzalkonium chloride compound.

4. A composition as recited in claim 1, wherein the at least one anti-infective agent comprises at least one benzalkonium chloride compound at a concentration in the range from about 0.01% to about 0.5% by volume of the treatment composition.

5. A composition as recited in claim 1, wherein the at least one anti-infective agent comprises at least one benzalkonium chloride compound at a concentration in the range from about 0.001% to about 0.05% by volume of the treatment composition.

6. A composition as recited in claim 1, wherein the at least one anti-infective agent is selected from the group consisting of a benzalkonium bromide compound and cetyl trimethylammonium bromide.

7. A composition as recited in claim 1, wherein the at least one anti-infective agent is selected from the group consisting of benzethonium chloride, methyl benzethonium chloride, cetyl pyridinium chloride, chloroxylenol, hexachlorophene, triclosan, and chlorhexidine.

8. A composition as recited in claim 1, wherein the at least one anti-infective agent comprises at least one quaternary ammonium chloride having an alkyl with 6–18 carbons.

9. A composition as recited in claim 1, wherein the carrier comprises isopropyl alcohol.

10. A composition as recited in claim 1, wherein the carrier comprises isopropyl alcohol and water.

11. A composition as recited in claim 1, wherein the carrier consists essentially of isopropyl alcohol and water.

12. A composition as recited in claim 1, wherein the carrier comprises isopropyl alcohol and water, the water being in an amount ranging from about 20% to about 40% by volume of the carrier.

13. A composition as recited in claim 1, wherein the carrier comprises an aqueous solution of isopropyl alcohol at a concentration of about 70% by volume of the carrier.

14. A composition as recited in claim 1, wherein the organohalide is comprised of at least one benzalkonium chloride compound at a concentration in the range from about 0.01% to about 0.5% by volume of the treatment composition, and wherein the carrier comprises an aqueous solution of isopropyl alcohol at a concentration of about 70% by volume of the carrier.

15. A composition as recited in claim 1, wherein the carrier comprises at least one alcohol selected from the group consisting of ethanol, methanol cetyl alcohol, and benzyl alcohol.

16. A composition as recited in claim 1, wherein the carrier comprises a compound selected from the group consisting of acetone, acetic acid, acetic anhydride, and mixtures thereof.

17. A composition as recited in claim 1, wherein the treatment composition is void of penetration inhibiting components.

18. A composition as recited in claim 1, wherein the treatment composition consists essentially of the organohalide and the carrier.

19. A composition as recited in claim 1, wherein the treatment composition enables rapid penetration into the disordered tissue in a manner such that the treatment composition is no longer visibly detectable on the disordered tissue within 2 minutes after application of the treatment composition onto the disordered tissue.

20. A treatment composition for application to and penetration into disordered tissue, the treatment composition comprising:
at least one anti-infective agent in a carrier, and wherein
the anti-infective agent comprises at least one benzalkonium chloride compound,
the carrier comprises isopropyl alcohol, and
the treatment composition is a liquid comprising a tissue penetrating component for penetrating skin in a rapid manner without rapidly diffusing beyond the skin.

21. A treatment composition for application to and penetration into disordered tissue, the treatment composition comprising:
at least one benzalkonium chloride compound in a carrier, and wherein
the carrier is comprised of a mixture of isopropyl alcohol and water, and
the treatment composition is a liquid comprising a tissue penetrating component for penetrating skin in a rapid manner without rapidly diffusing beyond the skin.

22. A composition as recited in claim 21, wherein the at least one benzalkonium chloride compound concentration in the treatment composition is in the range from about 0 01% to about 0.5% by volume of the treatment composition.

23. A composition as recited in claim 21, wherein the at least one benzalkonium chloride compound concentration in the treatment composition is in the range from about 0.001% to about 0.05% by volume of the treatment composition.

24. A composition as recited in claim 21, wherein the water is comprised in an amount ranging from about 20% to about 40% by volume of the carrier.

25. A composition as recited in claim 21, wherein the water is comprised in an amount ranging from about 20% to about 40% by volume of the carrier and the remainder of the carrier is comprised of isopropyl alcohol.

26. A composition as recited in claim 21, wherein the carrier comprises an aqueous solution of isopropyl alcohol at a concentration of about 70% by volume of the carrier.

27. A composition as recited in claim 21, wherein the at least one benzalkonium chloride compound concentration in the treatment composition is in the range from about 0.01% to about 0.5% by volume of the treatment composition, and wherein the carrier comprises an aqueous solution of isopropyl alcohol at a concentration of about 70% by volume of the carrier.

28. A composition as recited in claim 21, wherein the treatment composition is void of penetration inhibiting components.

29. A composition as recited in claim 21, wherein the treatment composition consists essentially of the at least one benzalkonium chloride compound and the carrier.

30. A composition as recited in claim 21, wherein the carrier further comprises at least one alcohol selected from the group consisting of ethanol, methanol, cetyl alcohol, and benzyl alcohol.

31. A composition as recited in claim 21, wherein the carrier further comprises a compound selected from the group consisting of acetone, acetic acid, acetic anhydride, and mixtures thereof.

32. A composition as recited in claim 21, wherein the treatment composition further comprises an anesthetic.

33. A treatment composition for application to and penetration into disordered tissue, the treatment composition comprising:
at least one benzalkonium chloride compound in a carrier, and wherein
the carrier is comprised of a mixture of isopropyl alcohol and water,
the treatment composition is a liquid comprising a tissue penetrating component for penetrating skin in a rapid manner without rapidly diffusing beyond the skin, and the treatment composition is substantially oil free such that there is essentially no residue remaining that is visibly detectable to any substantial degree after the treatment composition has been applied and absorbed.

34. A composition as recited in claim 33, wherein the at least one benzalkonium chloride compound concentration in the treatment composition is in the range from about 0.01% to about 0.5% by volume of the treatment composition.

35. A composition as recited in claim 33, wherein the at least one benzalkonium chloride compound concentration in the treatment composition is in the range from about 0.001% to about 0.05% by volume of the treatment composition.

36. A composition as recited in claim 33, wherein the water is comprised in an amount ranging from about 20% to about 40% by volume of the carrier.

37. A composition as recited in claim 33, wherein the carrier comprises an aqueous solution of isopropyl alcohol at a concentration of about 70% by volume of the carrier.

38. A composition as recited in claim 33, wherein the at least one benzalkonium chloride compound concentration in the treatment composition is in the range from about 0.01% to about 0.5% by volume of the treatment composition, and wherein the carrier comprises an aqueous solution of isopropyl alcohol at a concentration of about 70% by volume of the carrier.

39. A composition as recited in claim 33, wherein the treatment composition is void of penetration inhibiting components.

40. A treatment composition for application to and penetration into disordered tissue, the treatment composition comprising:
at least one benzalkonium chloride compound in a carrier, and wherein the carrier is comprised of a mixture of isopropyl alcohol and water, the water being in the range from about 20% to about 40% by volume of the carrier, and
the treatment composition is a liquid comprising a tissue penetrating component for penetrating skin in a rapid manner without rapidly diffusing beyond the skin.

41. A composition as recited in claim 40, wherein the at least one benzalkonium chloride compound concentration in the treatment composition is in the range from about 0.01% to about 0.5% by volume of the treatment composition.

42. A composition as recited in claim 40, wherein the at least one benzalkonium chloride compound concentration in the treatment composition is in the range from about 0.001% to about 0.05% by volume of the treatment composition.

43. A composition as recited in claim 40, wherein the carrier comprises an aqueous solution of isopropyl alcohol at a concentration of about 70% by volume of the carrier.

44. A composition as recited in claim 40, wherein the at least one benzalkonium chloride compound in the treatment composition is in the range from about 0.01% to about 0.5% by volume of the treatment composition, and wherein the carrier comprises an aqueous solution of isopropyl alcohol at a concentration of about 70% by volume of the carrier.

45. A composition as recited in claim 40, wherein the treatment composition is void of penetration inhibiting components.

46. A treatment composition for application to and penetration into disordered tissue, the treatment composition comprising:
   at least one benzalkonium chloride compound in a carrier, and wherein
      the carrier comprises an aqueous solution of isopropyl alcohol at a concentration of about 70% by volume of the carrier, and
      the treatment composition is a liquid comprising a tissue penetrating component for penetrating skin in a rapid manner without rapidly diffusing beyond the skin.

47. A composition as recited in claim 46, wherein the at least one benzalkonium chloride compound concentration in the treatment composition is in the range from about 0.01% to about 0.5% by volume of the treatment composition.

48. A composition as recited in claim 46, wherein the at least one benzalkonium chloride compound concentration in the treatment composition is in the range from about 0.001% to about 0.05% by volume of the treatment composition.

49. A composition as recited in claim 46, wherein the at least one benzalkonium chloride compound concentration in the treatment composition is about 0.013% by volume of the treatment composition.

50. A composition as recited in claim 46, wherein the treatment composition is void of penetration inhibiting components.

51. A system as recited in claim 1, wherein said organohalide comprises at least one of alkylbenzyldimethylammonium chloride, alkyldimethyl/ethylbenzylammonium chloride, n-alkyldimethylbenzylammonium chloride, diisobutylphenoxyethoxyethyldimethylbenzylammonium chloride, n—($C_{12}C_{14}C_{16}$) alkyl dimethylbenzylammonium chloride, didecyldimethylammonium chloride, dioctyldimethylammonium chloride, dialkyldimethylammonium chloride, dialkylmethylbenzylammonium chloride, octyldecyldimethylammonium chloride, lauryldimethylbenzylammonium chloride, o-benzyl-p-chlorophenol, didecyldimethylammonium chloride, dioctyldimethylammonium chloride, and alkyl ($C_{14}C_{12}C_{16}$) dimethylbenzylammonium chloride.

* * * * *

UNITED STATES PATENT AND TRADEMARK OFFICE
CERTIFICATE OF CORRECTION

PATENT NO.    : 6,414,032 B1
DATED         : July 2, 2002
INVENTOR(S)   : B. Ron Johnson It is certified that error appears in the above-identified patent and that said Letters Patent is hereby corrected as shown below:

Column 3,
Line 39, before "healing" change "in" to -- and --

Column 4,
Line 41, before "disordered" insert -- of --

Column 5,
Line 32, before "apparent" change "filly" to -- fully --

Column 7,
Line 34, after "second" insert -- . --
Line 42, before "applicator" delete "s"

Column 10,
Line 55, after "benzalkonium" insert -- chloride includes --
Line 56, after "benzene" insert -- ring --

Column 14,
Line 3, before "cold" change "titating" to -- treating --
Line 40, before "rapidly" change "to" to -- too --

Column 16,
Line 61, before "beyond." change "an" to -- and --

Column 17,
Line 46, after "alcohol" insert -- . --

Column 18,
Line 51, before "since tissue" change "use ful" to -- useful --
Line 53, after "thresholds." change "whether" to -- Whether --

UNITED STATES PATENT AND TRADEMARK OFFICE
CERTIFICATE OF CORRECTION

PATENT NO.    : 6,414,032 B1
DATED         : July 2, 2002
INVENTOR(S)   : B. Ron Johnson It is certified that error appears in the above-identified patent and that said Letters Patent is hereby corrected as shown below:

Column 20,
Line 67, before "As used" change "fodm." to -- foam. --

Column 21,
Line 47, after "tissue as" change "need" to -- needed --

Column 24,
Line 26, before "preferred" change "firther" to -- further --

Column 26,
Line 14, after "disclosed in" change "U.S. Pat. Nos. 4,183,684, 4,183,684" to
-- U.S. Patent No. 4,183,684. U.S. Patent No. 4,183,684 --
Line 47, after "may" change "provides" to -- provide --

Column 27,
Line 43, before "area" change "surfaces" to -- surface --

Column 28,
Line 28, before "surface" delete "a"

Column 29,
Line 3, before "immune" change "bodys" to -- body's --
Lines 40, 41 and 44, before "improvement" change "discemable" to -- discernable --
Lines 47, 50 and 53, before "improvement" change "discemable" to -- discernable --
Line 57, before "hereinbelow" change "provide" to -- provided --

UNITED STATES PATENT AND TRADEMARK OFFICE
CERTIFICATE OF CORRECTION

PATENT NO.    : 6,414,032 B1
DATED         : July 2, 2002
INVENTOR(S)   : B. Ron Johnson It is certified that error appears in the above-identified patent and that said Letters Patent is hereby corrected as shown below:

Column 34,
Line 10, after "thereof" insert -- . --
Lines 22 and 32, before "improvement" change "discemable" to -- discernable --

Signed and Sealed this

Twentieth Day of May, 2003

JAMES E. ROGAN
*Director of the United States Patent and Trademark Office*